(12) United States Patent
Ito et al.

(10) Patent No.: US 9,891,143 B2
(45) Date of Patent: Feb. 13, 2018

(54) CYLINDER TIP MOUNTING HEAD, AND HEAD DEVICE AND MOVEMENT DEVICE EACH USING SAME

(71) Applicant: YAMAHA HATSUDOKI KABUSHIKI KAISHA, Iwata-shi, Shizuoka-ken (JP)

(72) Inventors: Saburo Ito, Shizuoka (JP); Yukimasa Osada, Shizuoka (JP); Yohei Izume, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 0 days.

(21) Appl. No.: 15/445,089

(22) Filed: Feb. 28, 2017

(65) Prior Publication Data

US 2017/0167955 A1 Jun. 15, 2017

Related U.S. Application Data

(62) Division of application No. 15/317,595, filed as application No. PCT/JP2014/065967 on Jun. 17, 2014.

(51) Int. Cl.
*G01N 1/14* (2006.01)
*G01N 35/10* (2006.01)

(52) U.S. Cl.
CPC ............ *G01N 1/14* (2013.01); *G01N 35/1011* (2013.01); *G01N 35/1081* (2013.01); *G01N 2001/1427* (2013.01)

(58) Field of Classification Search
CPC ....... B01L 3/0227; B01L 3/0275; G01N 1/14; G01N 2001/1427; G01N 2001/1454;
(Continued)

(56) References Cited

U.S. PATENT DOCUMENTS

| 4,362,063 A | 12/1982 | Marteau d'Autry |
| 5,192,511 A | 3/1993 | Roach |

(Continued)

FOREIGN PATENT DOCUMENTS

| EP | 0 032 098 A1 | 7/1981 |
| EP | 0 155 087 A2 | 9/1985 |

(Continued)

OTHER PUBLICATIONS

The extended European search report issued by the European Patent Office dated Aug. 9, 2017, which corresponds to European Patent Application No. 17000537.5-1371 and is related to U.S. Appl. No. 15/445,089.

(Continued)

*Primary Examiner* — Brian R Gordon
(74) *Attorney, Agent, or Firm* — Studebaker & Brackett PC

(57) ABSTRACT

A cylinder tip mounting head includes: a shaft member; a first cylindrical rod having a cylindrical space, which is mounted to a lower end of the shaft member, which is configured to move in the up-down direction integrally with the shaft member; a stationary second cylindrical rod, which has a housing space for housing the first cylindrical rod so that the first cylindrical rod is movable in the up-down direction, the stationary second cylindrical rod including a syringe mounting portion; and a discharge rod housed in the cylindrical space in the first cylindrical rod, the discharge rod including a plunger mounting portion. The discharge rod is configured to coordinate with the movement of the shaft member in the up-down direction so that the plunger mounted to the discharge rod reciprocates in the tubular passage in the syringe to suck the object into the tubular passage and discharge the sucked object.

4 Claims, 17 Drawing Sheets

(58) Field of Classification Search
CPC .............. G01N 35/10; G01N 35/1011; G01N 35/1081; G01N 2035/103
See application file for complete search history.

(56) References Cited

U.S. PATENT DOCUMENTS

| | | | |
|---|---|---|---|
| 5,525,302 A * | 6/1996 | Astle | B01L 3/0279 422/511 |
| 6,143,252 A | 11/2000 | Haxo et al. | |
| 6,691,748 B1 | 2/2004 | Tajima | |
| 8,697,012 B2 * | 4/2014 | Ikushima | G01N 35/1074 422/509 |
| 8,932,542 B2 * | 1/2015 | Schaefer | B01L 9/06 422/509 |
| 2004/0050866 A1 * | 3/2004 | Ingenhoven | B01L 3/0241 222/135 |
| 2008/0293090 A1 * | 11/2008 | Powers | G01N 35/028 435/29 |
| 2009/0191097 A1 | 7/2009 | Hanafusa et al. | |
| 2010/0092342 A1 * | 4/2010 | Naumann | B01L 3/0227 422/400 |
| 2011/0268627 A1 * | 11/2011 | Warhurst | B01L 3/0227 422/511 |
| 2013/0017128 A1 * | 1/2013 | Silbert | G01N 35/0099 422/509 |
| 2013/0061694 A1 | 3/2013 | Saito et al. | |
| 2013/0074614 A1 | 3/2013 | Holmes et al. | |
| 2014/0112839 A1 * | 4/2014 | Richardson | G01N 35/0099 422/511 |
| 2014/0219887 A1 * | 8/2014 | Sheldon | B01L 3/0279 422/509 |
| 2015/0210437 A1 * | 7/2015 | Tajima | B01L 3/0275 222/1 |
| 2016/0023203 A1 * | 1/2016 | Richardson | B01L 3/0279 422/511 |

FOREIGN PATENT DOCUMENTS

| | | |
|---|---|---|
| EP | 1615013 A1 | 1/2006 |
| WO | 2013/166203 A2 | 11/2013 |

OTHER PUBLICATIONS

The extended European search report issued by the European Patent Office dated Jun. 19, 2017, which corresponds to European Patent Application No. 14894946.4-1371 and is related to U.S. Appl. No. 15/445,089.

* cited by examiner

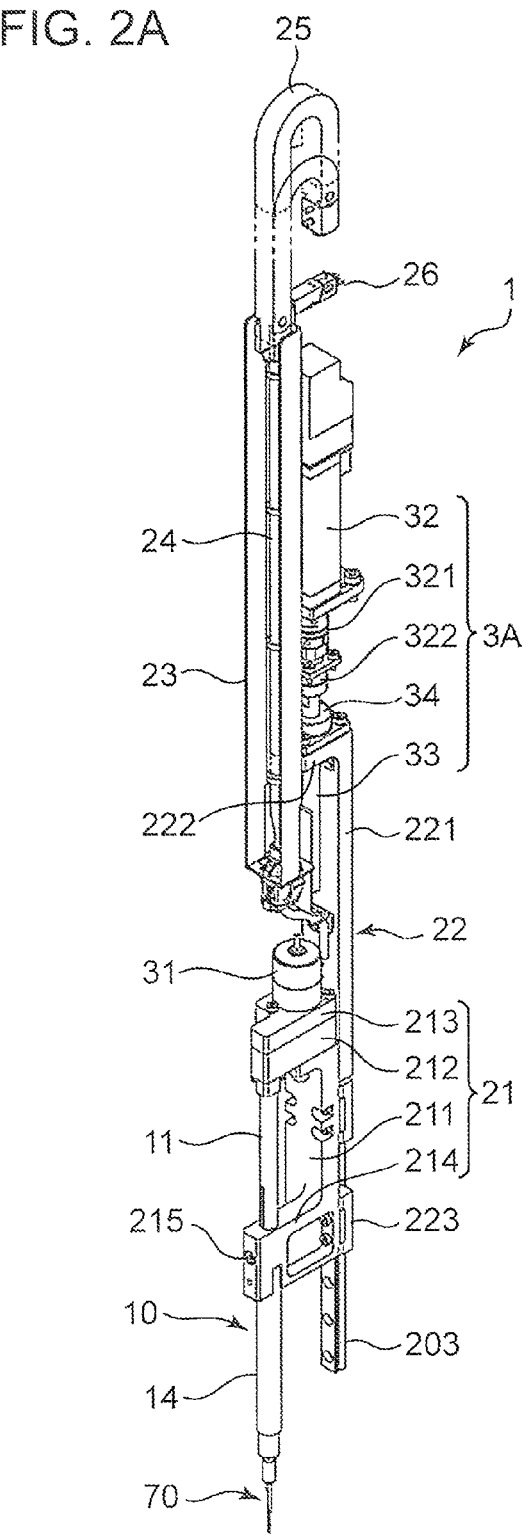
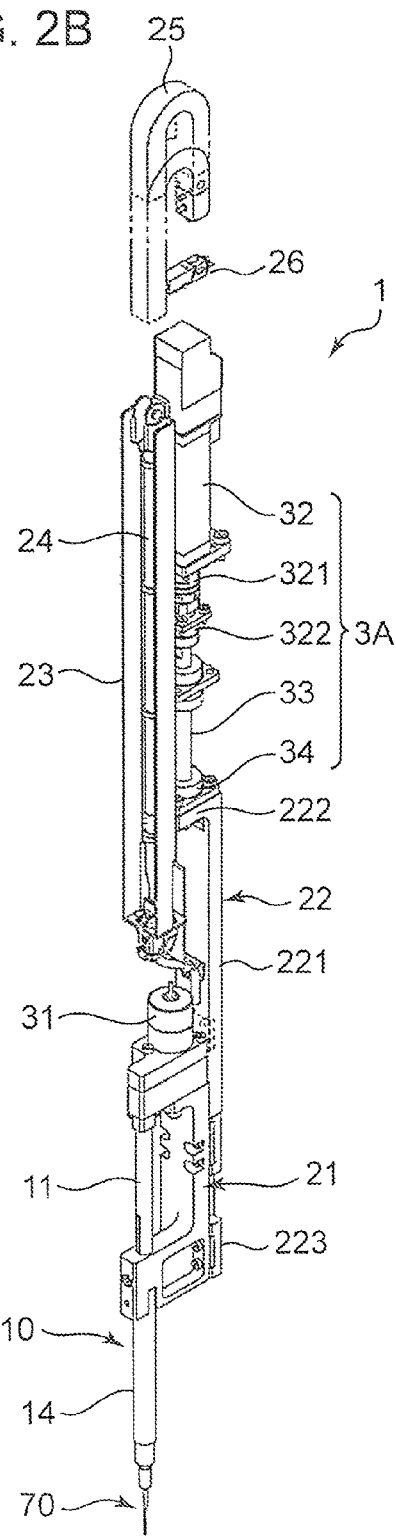
FIG. 2A
FIG. 2B

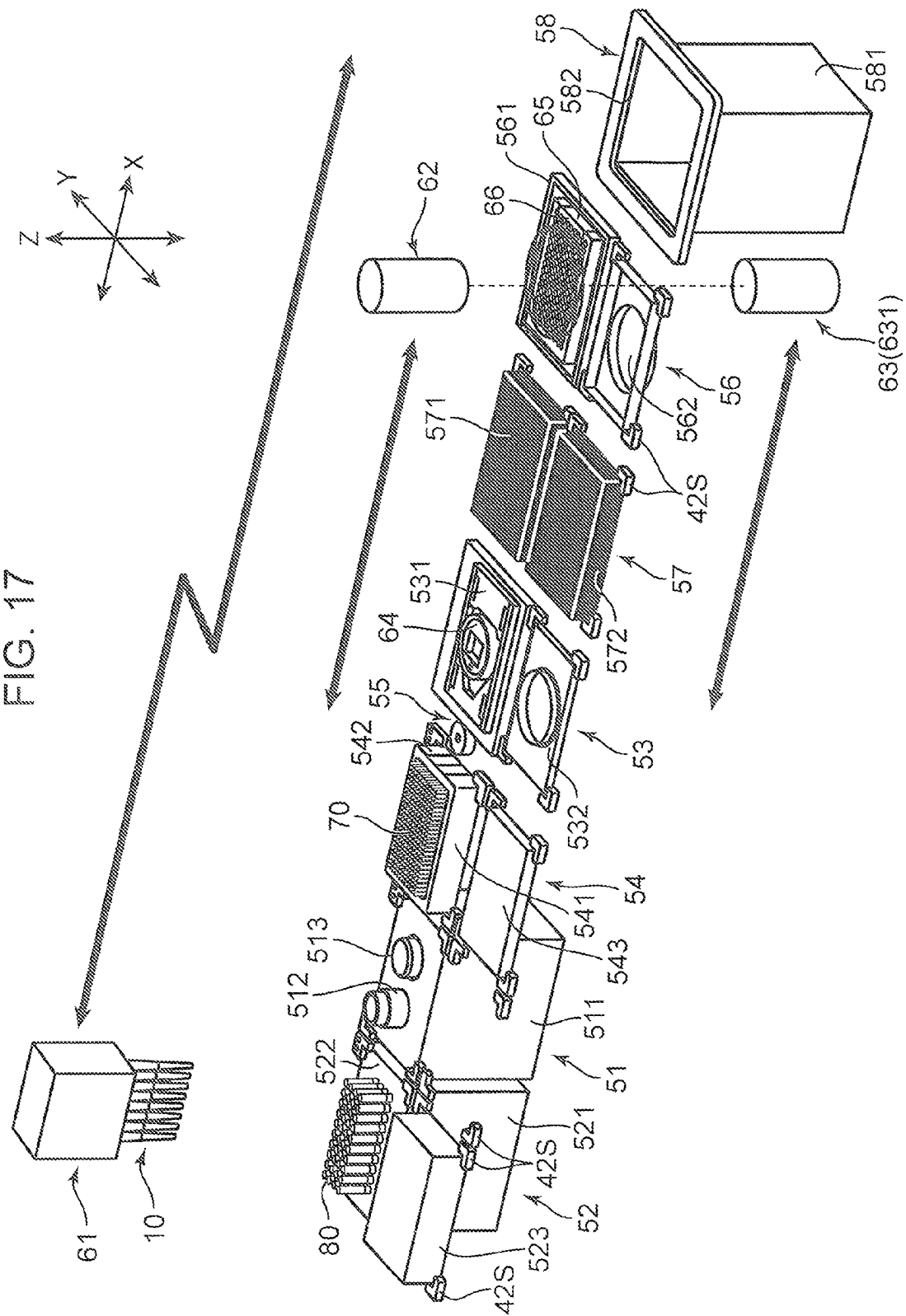

CYLINDER TIP MOUNTING HEAD, AND HEAD DEVICE AND MOVEMENT DEVICE EACH USING SAME

CROSS REFERENCE TO RELATED APPLICATION

This application is a Divisional Application of U.S. patent application Ser. No. 15/317,595 filed Dec. 9, 2016, which claims benefit of priority to International Patent Application No. PCT/JP2014/065967 filed Jun. 17, 2014, the entire content of which is incorporated herein by reference.

TECHNICAL FIELD

The present disclosure relates to a head to be mounted with a cylinder tip configured to suck an object, such as a cell aggregate, and discharge the sucked object, and to a head device and a movement device for an object each using the head.

BACKGROUND

Movement devices configured to move a certain object from one container to another container are required in various technical fields. For example, there is a moving device configured such that, in a case where there are a first container storing a large number of moving objects such as compact parts, organic or inorganic fragments or particles, and cells, and a second container receiving the moving objects, some of the moving objects are extracted from the first container and moved to the second container. Such a movement device needs a suction tip configured to suck an object from the first container and discharge the sucked object to the second container.

Japanese Unexamined Patent Publication No. 2009-34013 discloses a technology of sucking a cell aggregate, which serves as the moving object, from a dispenser well with use of a suction tip (micropipette) and discharging the sucked cell aggregate to a cell Petri dish. A cell aggregate is held in a liquid, and when the suction tip is used to suck the cell aggregate, a distal opening portion of the suction tip is immersed into the liquid. Accordingly, the suction tip may be required to be discarded after a single set of suction and discharge.

In the work of moving an object, there has been a requirement for highly automating a series of operations including suction and discharge of the object using the suction tip. At present, however, the suction tip is manually operated, or automation is limited to such an extent that only a suction force generation mechanism is attached to the suction tip. It cannot therefore be said that the movement work has high work efficiency at present.

SUMMARY

It is an object of the present disclosure to provide a head capable of highly automating works of sucking an object and discharging the sucked object with use of a cylinder tip, and a head device and a movement device for an object each using the head.

A cylinder tip mounting head according to one aspect of the present disclosure is to be mounted with a cylinder tip, the cylinder tip including: a syringe including a tubular passage inside serving as a suction path for an object; and a plunger configured to reciprocate in the tubular passage. The head includes: a shaft member configured to move in an up-down direction; a first cylindrical rod, which is mounted to a lower end of the shaft member, which is configured to move in the up-down direction integrally with the shaft member, and which has a cylindrical space formed therein; a stationary second cylindrical rod, which has a housing space for housing the first cylindrical rod so that the first cylindrical rod is movable in the up-down direction, the stationary second cylindrical rod including, at a lower end, a syringe mounting portion to which a base end portion of the syringe is to be fitted; and a discharge rod housed in the cylindrical space in the first cylindrical rod, the discharge rod including, at a lower end, a plunger mounting portion to which a base end portion of the plunger is to be fitted. The discharge rod is configured to coordinate with the movement of the shaft member in the up-down direction so that the plunger mounted to the discharge rod reciprocates in the tubular passage in the syringe to suck the object into the tubular passage and discharge the sucked object.

A head device according to another aspect of the present disclosure includes: the cylinder tip mounting head; a motor configured to generate the rotary drive force; a transmission mechanism configured to transmit the rotary drive force to the shaft member; a frame member configured to hold the motor, the transmission mechanism, and the second cylindrical rod; and a control unit configured to control drive of the motor to control the movement of the shaft member in the up-down direction.

A movement device according to still another aspect of the present disclosure includes: the head device including a mechanism configured to move the cylinder tip mounting head in an up-down direction as a whole; a first container configured to store an object; a second container configured to receive the object; and a head moving mechanism configured to move the head device in a horizontal direction between the first container and the second container.

Objects, features and advantages of the present disclosure become more apparent from the following detailed description and the accompanying drawings.

BRIEF DESCRIPTION OF THE DRAWINGS

FIG. 2A and FIG. 2B are perspective views of the head device, in which FIG. 2A is a view illustrating a state in which a head is raised in a Z-axis direction and FIG. 2B is a view illustrating a state in which the head is lowered in the Z-axis direction.

FIG. 17 is a perspective view illustrating components of a cell movement line in the cell moving device.

DETAILED DESCRIPTION

A cylinder tip mounting head and a head device using the head according to embodiments of the present disclosure are now described in detail with reference to the accompanying drawings. In this embodiment, the case where an object to be sucked and discharged by a cylinder tip is a biological cell, in particular, a cell aggregate, is described. Note that the object is not limited to a cell aggregate, and may be a compact electronic or mechanical part, an organic or inorganic fragment or particle, or a pellet.

Figure 1:
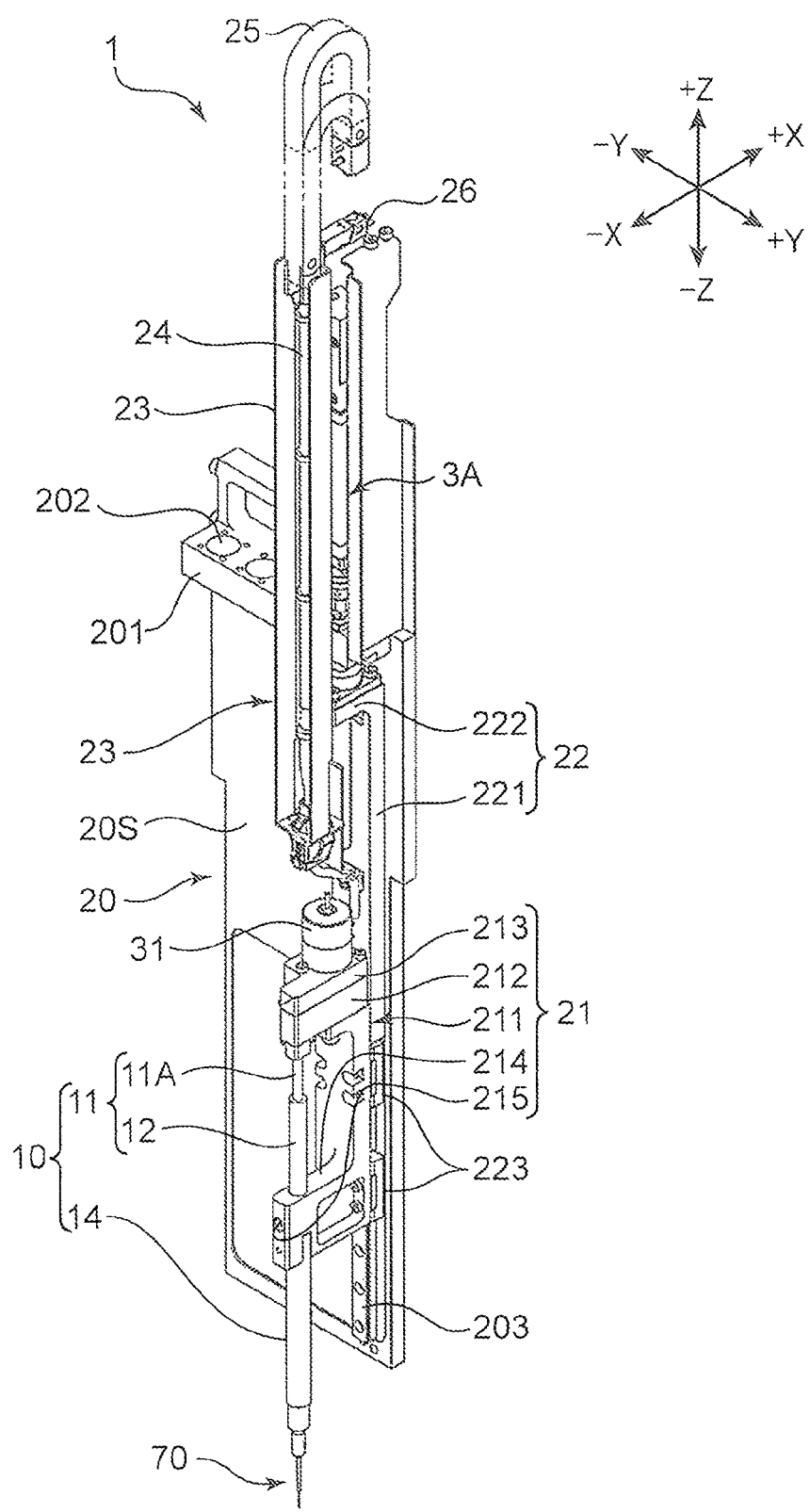
FIG. 1 is a perspective view illustrating an appearance of a head device according to an embodiment of the present disclosure in a state in which the head device is assembled to a unit frame.
Figure 3:
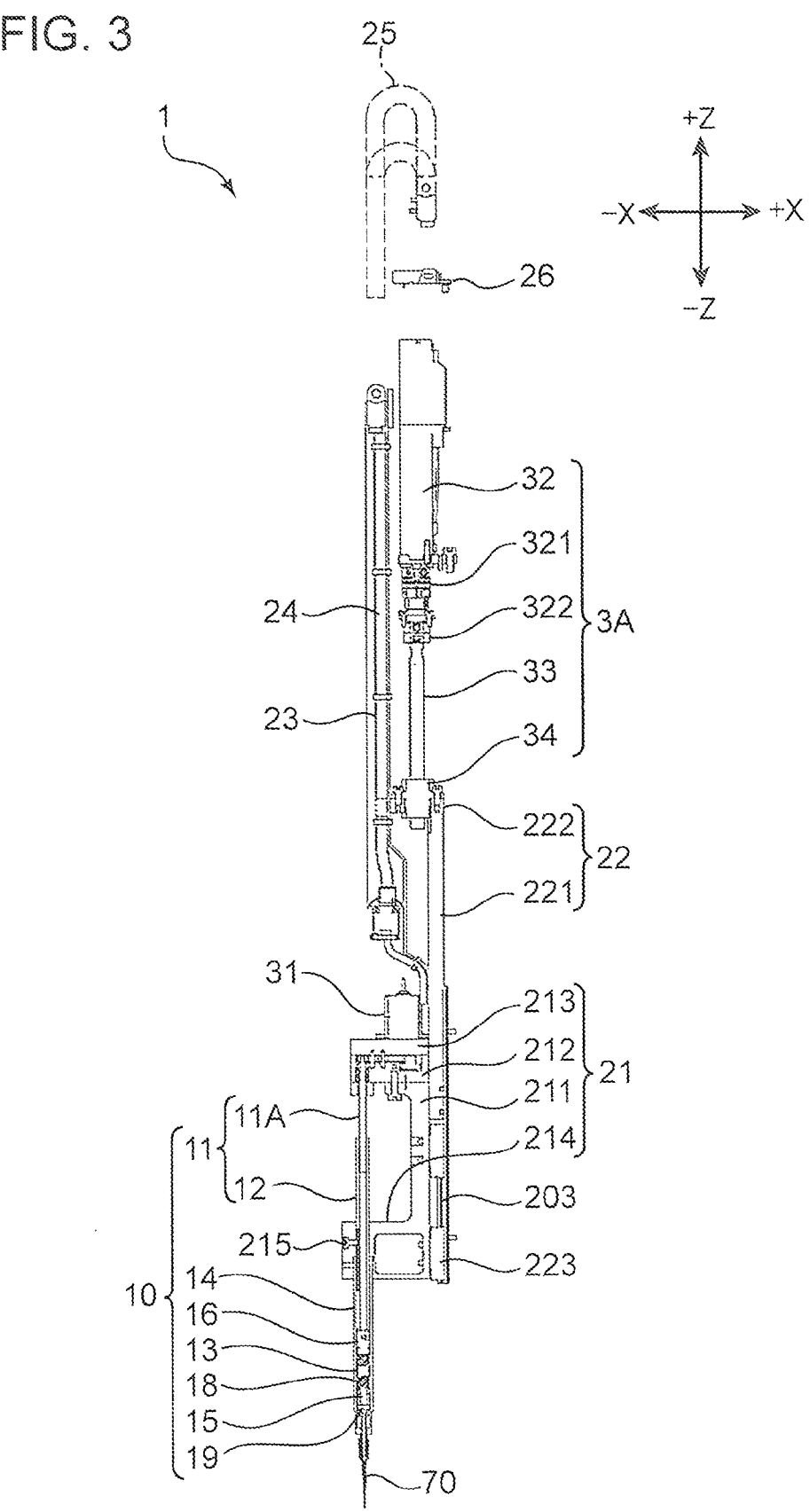
FIG. 3 is a side cross-sectional view of the head device.

FIG. 1 is a perspective view illustrating an appearance of a head device 1 according to an embodiment of the present disclosure in a state in which the head device 1 is assembled to a unit frame 20. FIG. 2A and FIG. 2B are perspective views of the head device 1 alone, and FIG. 3 is a side cross-sectional view of the head device 1. The head device 1 includes a head 10 to which a cylinder tip 70 is mounted, a first frame 21 (frame member) configured to hold the head 10, a second frame 22 to which the first frame 21 is mounted and which is configured to move in an up-down direction (Z direction), a first motor 31 (motor) mounted to the first frame 21 and configured to drive the head 10, and a ball screw device 3A configured to move the second frame 22 in the Z direction. A plurality of the head devices 1 are assembled to the unit frame 20 to form a head unit.

The head 10 has the cylinder tip 70 mounted thereto at a lower end thereof, and causes the cylinder tip 70 to perform the operation of sucking and discharging an object. The head 10 includes a shaft member 11 configured to move in the up-down direction, a first cylindrical rod 13 mounted to a lower end of the shaft member 11 (second screw shaft 12) and configured to move in the up-down direction integrally with the shaft member 11, a stationary second cylindrical rod 14 configured to house the first cylindrical rod 13 so that the first cylindrical rod 13 is movable in the up-down direction, and a discharge rod 15 housed in the first cylindrical rod 13. The detailed structure of the head 10 is described later in detail with reference to FIG. 7 and FIG. 8.

The unit frame 20 is a flat plate-shaped metal frame that has a holding flat surface 20S extending in the YZ directions. FIG. 1 illustrates the state in which one head device 1 is assembled, but the unit frame 20 in this embodiment is capable of holding four head devices 1 in a manner that the head devices 1 are arranged side by side in the Y direction. A holder portion 201 extending in the Y direction is provided in the vicinity of a +Z-direction end portion (vicinity of an upper end) of the holding flat surface 20S in a protruding manner. The holder portion 201 is provided with four through holes 202 passing through the holder portion 201 in the Z direction. Upper end bearings 322 of a screw shaft 33 described next are fitted into the through holes 202, and the upper end bearing 322 are fixed to the holder portion 201 with screws. A guide rail 203 extending in the Z direction is mounted in a region from the center of the holding flat surface 20S to the vicinity of a −Z-direction end portion (vicinity of a lower end) of the holding flat surface 20S. The guide rail 203 is arranged in order to guide the movement of the first frame 21 in the Z direction.

The ball screw device 3A includes a second motor 32, a coupling 321, the upper end bearings 322, the screw shaft 33, and a nut member 34, which are arranged in the Z direction. The second motor 32 is a motor configured to generate a rotary drive force for rotating the screw shaft 33 about its axis in the forward and reverse directions. The coupling 321 is a member configured to couple an output shaft of the second motor and an upper end of the screw shaft 33 to each other. The upper end bearings 322 rotatably support an upper end of the screw shaft 33. The upper end bearing 322 includes a cylindrical portion and a flange portion. The cylindrical portion is fitted into the through hole 202, and the flange portion is held by an upper surface of the holder portion 201. The screw shaft 33 extends in the Z direction, and a circumferential surface thereof is threaded with a male screw. The nut member 34 has a female screw on an inner surface thereof, and is screwed with the screw shaft 33. When the screw shaft 33 rotates in the forward or reverse direction, the nut member 34 moves upward (+Z) or downward (−Z).

The first frame 21 serves to hold the first motor 31, to hold the upper end bearings of the shaft member 11, and to hold the second cylindrical rod 14 in a fixed manner. The detailed structure of the first frame 21 is described in detail later with reference to FIG. 7.

The second frame 22 is an L-shaped frame that includes a vertical portion 221 extending in the Z direction and a horizontal portion 222 protruding from an upper end of the vertical portion 221 in the −X direction. The first frame 21 is fixed to the vicinity of a lower end of the vertical portion 221. The horizontal portion 222 is provided with a through hole in the Z direction, and the nut member 34 of the ball screw device 3A is fixed to the horizontal portion 222 in the state in which the nut member 34 is fitted into the through hole. Thus, when the screw shaft 33 is driven to rotate so that the nut member 34 moves upward or downward, the second frame 22 and the first frame 21 coupled to the second frame 22 also move upward or downward in a coordinated manner. FIG. 2A is a view illustrating a state in which the first and second frames 21 and 22 are raised, and FIG. 2B is a view illustrating a state in which the first and second frames 21 and 22 are lowered.

A cable tray 23 is mounted to a −X-side end surface of the horizontal portion 222. The cable tray 23 holds a power supply cable 24 for the first motor 31. The vicinity of an upper end of the power supply cable 24 is protected by a bent protection member 25. The bent protection member 25 is a part that curves to be convex in an upward direction, and is deformed following the vertical movement of the second frame 22. A Z-axis sensor 26 is arranged to be opposed to a vertical part in the vicinity of a lower end of the bent protection member 25. The Z-axis sensor 26 is a sensor for detecting a Z-direction position of the second frame 22 and accordingly a Z-direction position of the head 10.

Figure 4:
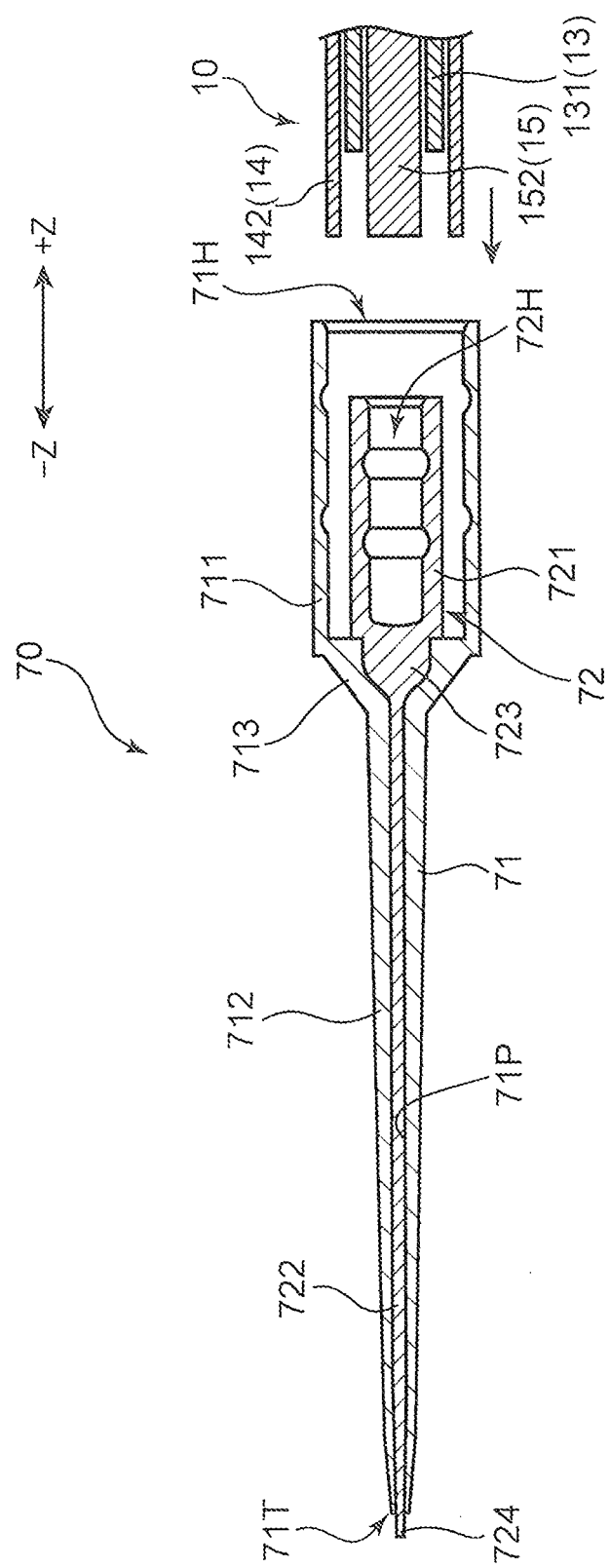
FIG. 4 is a cross-sectional view of a cylinder tip.
Figure 5:
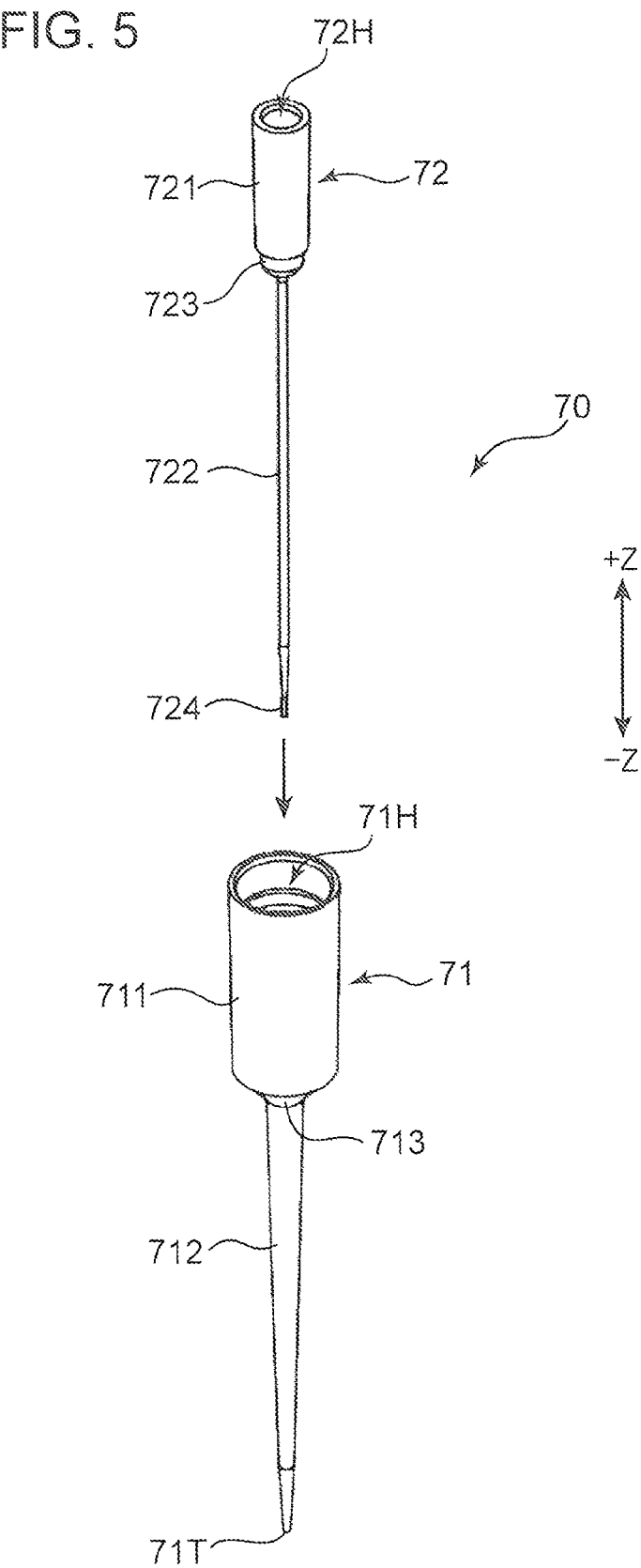
FIG. 5 is an exploded perspective view of the cylinder tip.

Subsequently, the cylinder tip 70 to be mounted to the head 10 according to this embodiment is described. FIG. 4 is a cross-sectional view of the cylinder tip 70, and FIG. 5 is an exploded perspective view of the cylinder tip 70. The cylinder tip 70 includes a syringe 71 having a tubular passage 71P inside serving as a suction path for a cell aggregate (object), and a plunger 72 configured to reciprocate in the tubular passage 71P while sliding in contact with an inner circumferential wall of the syringe 71 that defines the tubular passage 71P.

The syringe 71 includes a syringe base end portion 711 formed of a cylindrical body having a large diameter, a syringe main body portion 712 formed of an elongated cylindrical body having a small diameter, and a tapered cylinder portion 713 connecting the base end portion 711 and the main body portion 712 to each other. The tubular passage 71P is formed in the syringe main body portion 712. A suction port 71T (serving also as a discharge port) is provided in a distal end of the syringe main body portion 712. The plunger 72 includes a plunger base end portion 721 formed of a cylindrical body, a needle-shaped plunger main body portion 722, and a hemisphere portion 723 connecting the base end portion 721 and the main body portion 722 to each other.

The syringe base end portion 711 has a cylindrical hollow portion 71H. The outer diameter of the plunger base end portion 721 is set to be smaller than the inner diameter of the hollow portion 71H by a predetermined length. The outer diameter of the plunger main body portion 722 is set to be slightly smaller than the inner diameter of the tubular passage 71P. Further, the shape of an inner circumferential surface of the tapered cylinder portion 713 conforms to the curved surface shape of an outer circumferential surface of the hemisphere portion 723. The plunger 72 is assembled to the syringe 71 in a manner that the plunger base end portion 721 is housed in the hollow portion 71H and the plunger main body portion 722 is inserted into the tubular passage 71P in the syringe main body portion 712.

FIG. 5 illustrates the state in which the plunger 72 is removed from the syringe 71, but FIG. 4 illustrates the state in which the plunger main body portion 722 is inserted into the syringe main body portion 712 most deeply, that is, the state in which the plunger 72 is lowered most. In this case, the hemisphere portion 723 is completely received in a cavity in the tapered cylinder portion 713. The length of the plunger main body portion 722 is slightly larger than the length of the syringe main body portion 712. In the state in FIG. 4, a distal end portion 724 protrudes from the suction port 71T. Further, a gap exists between an inner circumferential surface of the syringe base end portion 711 and an outer circumferential surface of the plunger base end portion 721.

The plunger 72 can move in the +Z direction (up direction) with respect to the syringe 71 from the state in FIG. 4. When the plunger 72 moves in the +Z direction by a predetermined length, the distal end portion 724 of the plunger main body portion 722 sinks in the tubular passage 71P. In this case, a suction force can be generated from the suction port 71T to suck a liquid (in this embodiment, a cell culture liquid) around the suction port 71T into the tubular passage 71P. After the suction, when the plunger 72 is moved in the −Z direction (downward), the liquid sucked into the tubular passage 71P can be discharged from the suction port 71T.

A mounting hole 72H formed of a cylindrical hollow space, which has an opening at a +Z-direction end surface thereof, is provided in the plunger base end portion 721. A plunger mounting portion 152 of the discharge rod 15 described later is press-fitted into the mounting hole 72H. The press-fitting enables the discharge rod 15 and the plunger 72 to be integrated with each other. A +Z-direction end surface of the plunger base end portion 721 is opposed to a −Z-direction end surface of the first cylindrical rod 13. A syringe mounting portion 142 of the stationary second cylindrical rod 14 is press-fitted into the hollow portion 71H in the syringe base end portion 711.

Subsequently, the operation of sucking and discharging a cell aggregate C by the cylinder tip 70 is described with reference to FIGS. 6A to 6E. A case is described in which the cylinder tip 70 is used to suck a cell aggregate C present in a cell culture liquid Lm1 stored in a first container C1 and discharge the cell aggregate C into a cell culture liquid Lm2 stored in a second container C2.

Figure 6:
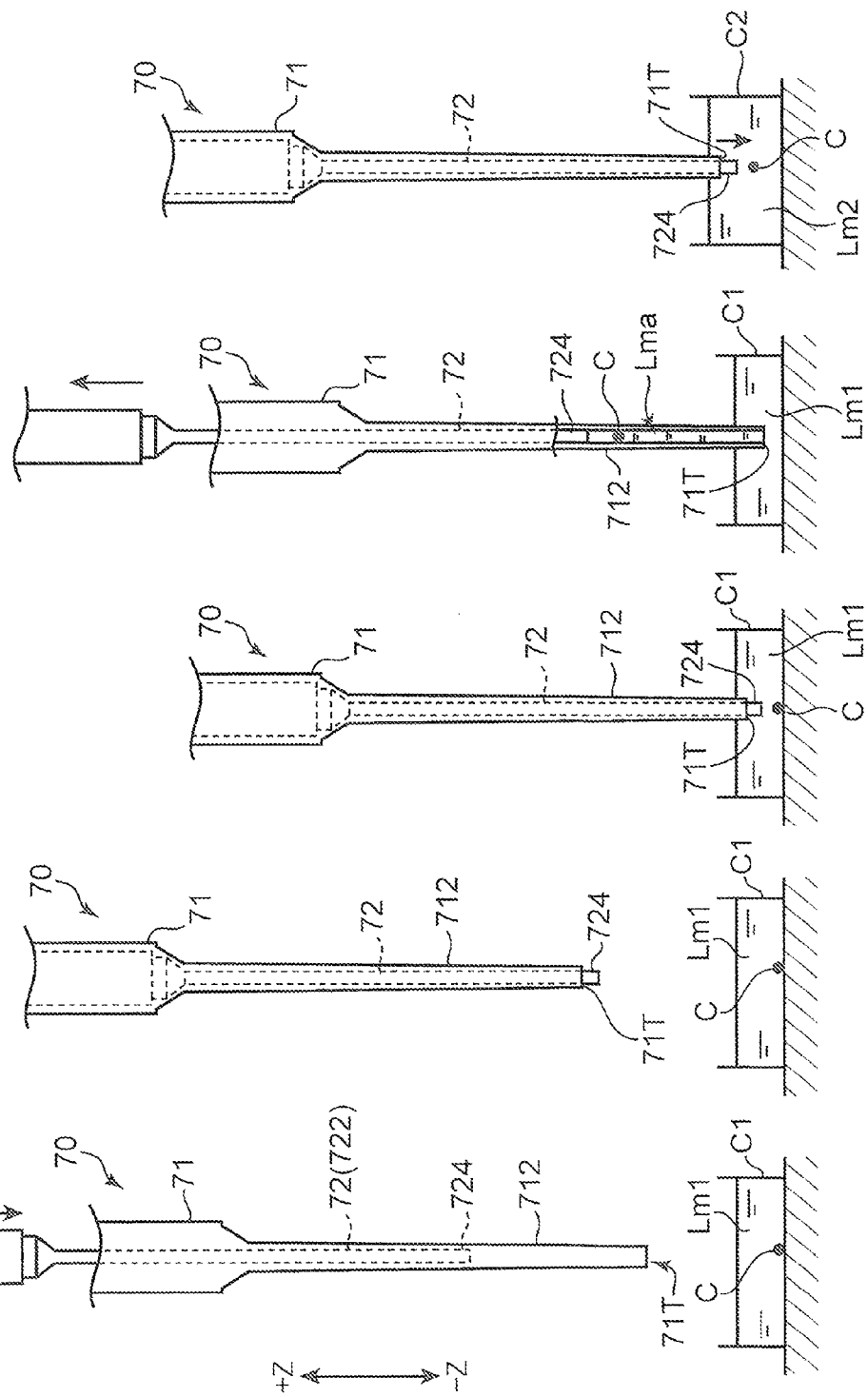
FIGS. 6A to 6E are schematic diagrams illustrating an operation of sucking and discharging a cell aggregate by the cylinder tip.

The operation of sucking and discharging a cell aggregate C by the cylinder tip 70 includes the following Steps 1 to 6.
(Step 1) As illustrated in FIG. 6A, the cylinder tip 70 is moved directly above a cell aggregate C to be sucked.
(Step 2) If the plunger 72 has moved upward (+Z direction) relative to the syringe 71 and the distal end portion 724 of the plunger main body portion 722 has sunk into the syringe main body portion 712, the plunger 72 is moved to the lowest position (−Z direction) so that the distal end portion 724 protrudes from the suction port 71T as illustrated in FIG. 6B. Specifically, the state in which no air is present in the tubular passage 71P in the syringe main body portion 712 is established.
(Step 3) After that, as illustrated in FIG. 6C, the cylinder tip 70 is lowered as a whole so that the suction port 71T enters the cell culture liquid Lm1 in the first container C1. In this case, the suction port 71T is made closer to the cell aggregate C as much as possible.
(Step 4) Subsequently, as illustrated in FIG. 6D, the plunger 72 is moved upward by a predetermined height. This operation generates a suction force at the suction port 71T so that the cell aggregate C and part of a cell culture liquid Lma are sucked into the syringe main body portion 712. In this state, the cylinder tip 70 is raised as a whole to be moved to the arrangement position of the second container C2.
(Step 5) Then, as illustrated in FIG. 6E, the cylinder tip 70 is lowered as a whole until the suction port 71T enters the cell culture liquid Lm2 in the second container C2. After that, the plunger 72 at a predetermined height position is lowered until the distal end portion 724 protrudes from the suction port 71T. This lowering operation discharges the cell aggregate C into the cell culture liquid Lm2 in the second container C2.
(Step 6) Although the illustration is omitted, the cylinder tip 70 is separated from the head 10. The reason is that the cylinder tip 70 that has been once immersed in the cell culture liquid cannot be used again in many cases and a new cylinder tip 70 needs to be mounted again to the head 10. It should be understood that the cylinder tip 70 is not necessarily required to be replaced for every use, and the same cylinder tip 70 may be used a plurality of times (for example, 20 to 30 times of suction and discharge) until a problem occurs in its use due to contamination by cell components, and thereafter the cylinder tip 70 may be separated from the head 10.

Figure 7:
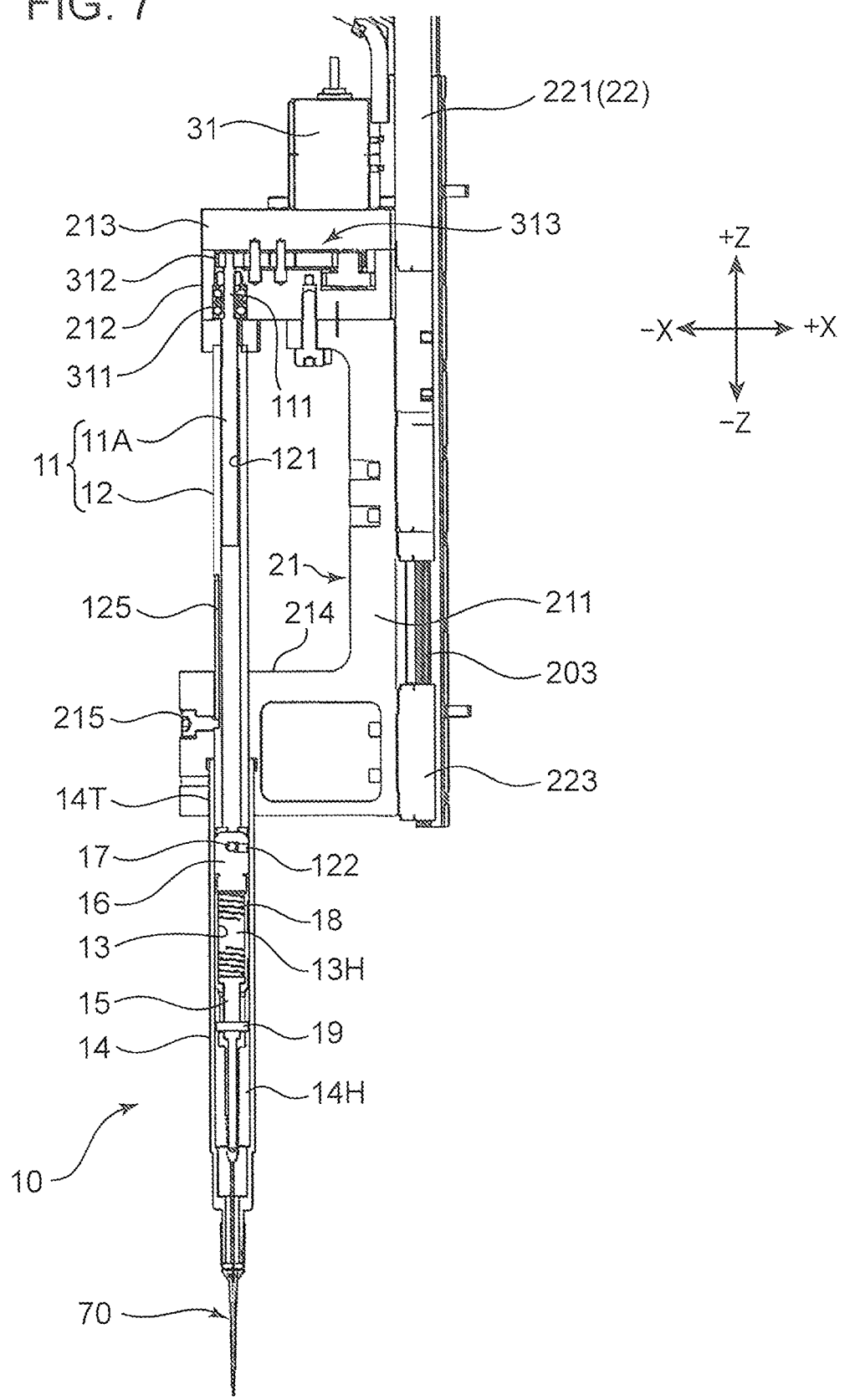
FIG. 7 is a cross-sectional view of the head and its vicinity.
Figure 8:
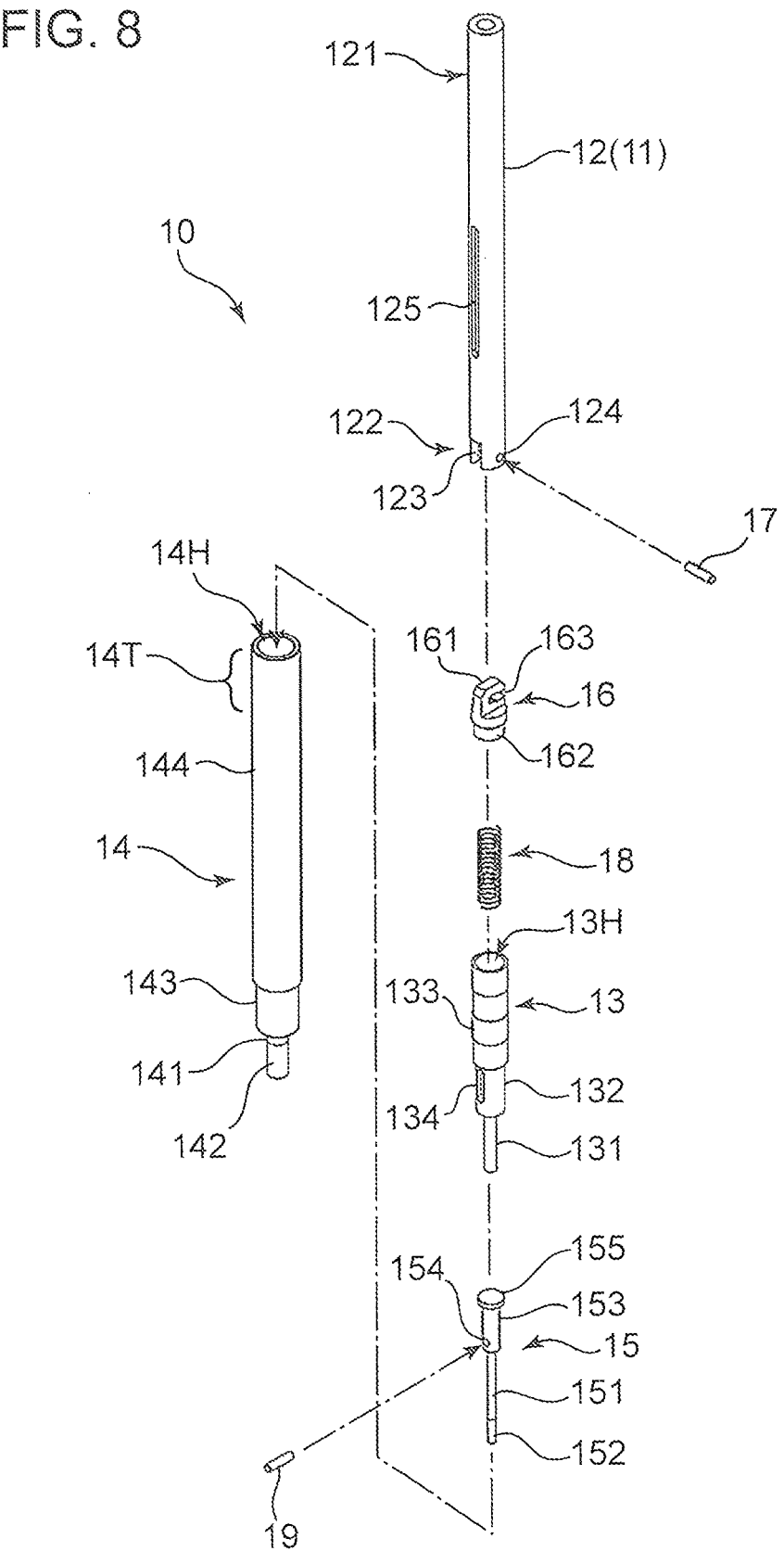
FIG. 8 is an exploded perspective view of the head.

The head device 1 (head 10) in this embodiment has the function of automatically performing Steps 1 to 6 using the cylinder tip 70 described above. The detailed structure of the head 10 is now described. FIG. 7 is a cross-sectional view of the head 10 and its vicinity (first frame 21). FIG. 8 is an exploded perspective view of the head 10.

The head 10 includes the shaft member 11, the first cylindrical rod 13, the second cylindrical rod 14, the discharge rod 15, a coupler piece 16, a coupler pin 17, a coil spring 18 (elastic member), and a stopper 19, which are arranged in the Z direction. The first frame 21 includes a vertical frame 211 extending in the up-down direction (Z direction), a holding frame 212 that is assembled to an upper end of the vertical frame 211 and protrudes in the −X direction, a motor support frame 213 assembled onto the holding frame 212, and a rod holding frame 214 that protrudes in the −X direction from a lower end of the vertical frame 211.

The shaft member 11 is a screw shaft whose outer circumferential surface is threaded with a male screw. The shaft member 11 includes a first screw shaft 11A to be applied a rotary drive force and a cylindrical second screw shaft 12 to be screwed with the first screw shaft 11A. The second screw shaft 12 includes an upper end part 121 threaded with a female screw to be engaged with the male screw of the first screw shaft 11A, and a lower end portion 122 to which the first cylindrical rod 13 is to be mounted via the coupler piece 16. When the first screw shaft 11A rotates in the forward direction or the reverse direction about its axis, the second screw shaft 12 moves in the down direction (−Z direction) or the up direction (+Z direction). An upper end portion 111 of the first screw shaft 11A is rotatably supported by bearings 311. Further, an input gear 312 is mounted to the uppermost end of the first screw shaft 11A.

The first motor 31 is a motor configured to generate a rotary drive force for rotating the first screw shaft 11A about its axis in the forward direction or the reverse direction, and is mounted to the motor support frame 213. A gear unit 313 (transmission mechanism) is interposed between an output shaft of the first motor 31 and the input gear 312. The rotary drive force is transmitted to the input gear 312 via the gear unit 313 to rotate the first screw shaft 11A. The bearing 311 and the gear unit 313 are held by the holding frame 212.

A lower end portion 122 of the second screw shaft 12 is provided with slit 123 and pinholes 124. The slits 123 are each formed by cutting part of a cylindrical circumferential wall of the lower end portion 122 into a rectangular shape. FIG. 8 illustrates only one slit 123, but a similar slit exists in the circumferential wall opposed to the slit 123. The pinholes 124 are formed in a pair of circumferential wall portions where the slits 123 are not formed, at positions shifted from those of the slits 123 by 90 degrees in the circumferential direction. In the pinholes 124, the coupler pin 17 configured to mechanically couple the second screw shaft 12 and the coupler piece 16 to each other is inserted.

A long groove 125 extending in the up-down direction is formed in a circumferential wall of the second screw shaft 12 in the vicinity of an intermediate part in the up-down direction. A distal end portion of the guide screw 215 is fitted into the long groove 125. The guide screw 215 includes a part to be screwed to the rod holding frame 214, and the distal end portion continuously provided on this part. As described above, when the first screw shaft 11A rotates about its axis, the second screw shaft 12 moves in the up-down direction. In this case, the second screw shaft 12 does not rotate about its axis due to the guide screw 215 fitted into the long groove 125, but the movement of the second screw shaft 12 in the up-down direction is guided. The length of the long groove 125 in the up-down direction corresponds to the movement range of the second screw shaft 12.

The coupler piece 16 includes a hook portion 161 located on the upper side and a screw portion 162 located on the lower side. The hook portion 161 has such a width that can be housed in the slits 123, and includes a receiving groove 163 capable of sandwiching the coupler pin 17. The coupler pin 17 passes through the pair of pinholes 124 and the receiving groove 163 in the state in which the hook portion 161 is housed in the slits 123, thereby coupling the coupler piece 16 to the lower end portion 122 of the second screw shaft 12.

The first cylindrical rod 13 is a cylindrical member having a cylindrical space 13H inside for housing the discharge rod 15 and the coil spring 18. A screw groove is formed in the vicinity of an upper end of an inner wall of the first cylindrical rod 13 that defines the cylindrical space 13H. When the screw groove is screwed with the screw portion 162 of the coupler piece 16, the first cylindrical rod 13 is connected to the second screw shaft 12 (shaft member 11) via the coupler piece 16. As a result, the first cylindrical rod 13 can move in the up-down direction integrally with the second screw shaft 12.

The first cylindrical rod 13 has a shape whose outer diameter is increased from the lower side to the upper side in three stages. The first cylindrical rod 13 includes a first cylinder portion 131 that is located at the lowest position and has the smallest outer diameter, a second cylinder portion 132 that is continuously provided above the first cylinder portion 131 and has a diameter larger than that of the first cylinder portion 131, and a third cylinder portion 133 that is continuously provided above the second cylinder portion 132 and has a diameter larger than that of the second cylinder portion 132. A long hole 134 extending in the up-down direction is formed in a circumferential wall of the second cylinder portion 132.

The discharge rod 15 is a member for operating the plunger 72 in the up-down direction. The discharge rod 15 is housed in the cylindrical space 13H in the first cylindrical rod 13 so as to be movable in the up-down direction relative to the first cylindrical rod 13. The discharge rod 15 also has a shape whose outer diameter is increased from the lower side to the upper side in three stages. The discharge rod 15 includes a first columnar portion 151 that is located at the lowest position and has the smallest first outer diameter, a second columnar portion 153 that is continuously provided above the first columnar portion 151 and has a second outer diameter larger than the first outer diameter, and a third columnar portion 155 that is continuously provided above the second columnar portion 153 and has a third outer diameter larger than the second outer diameter. The vicinity of a lower end of the first columnar portion 151 is a plunger mounting portion 152 onto which the plunger base end portion 721 of the plunger 72 is to be fitted. Further, a stopper hole 154 passing through the second columnar portion 153 in the lateral direction is formed in the vicinity of a lower end of the second columnar portion 153.

Figure 10:
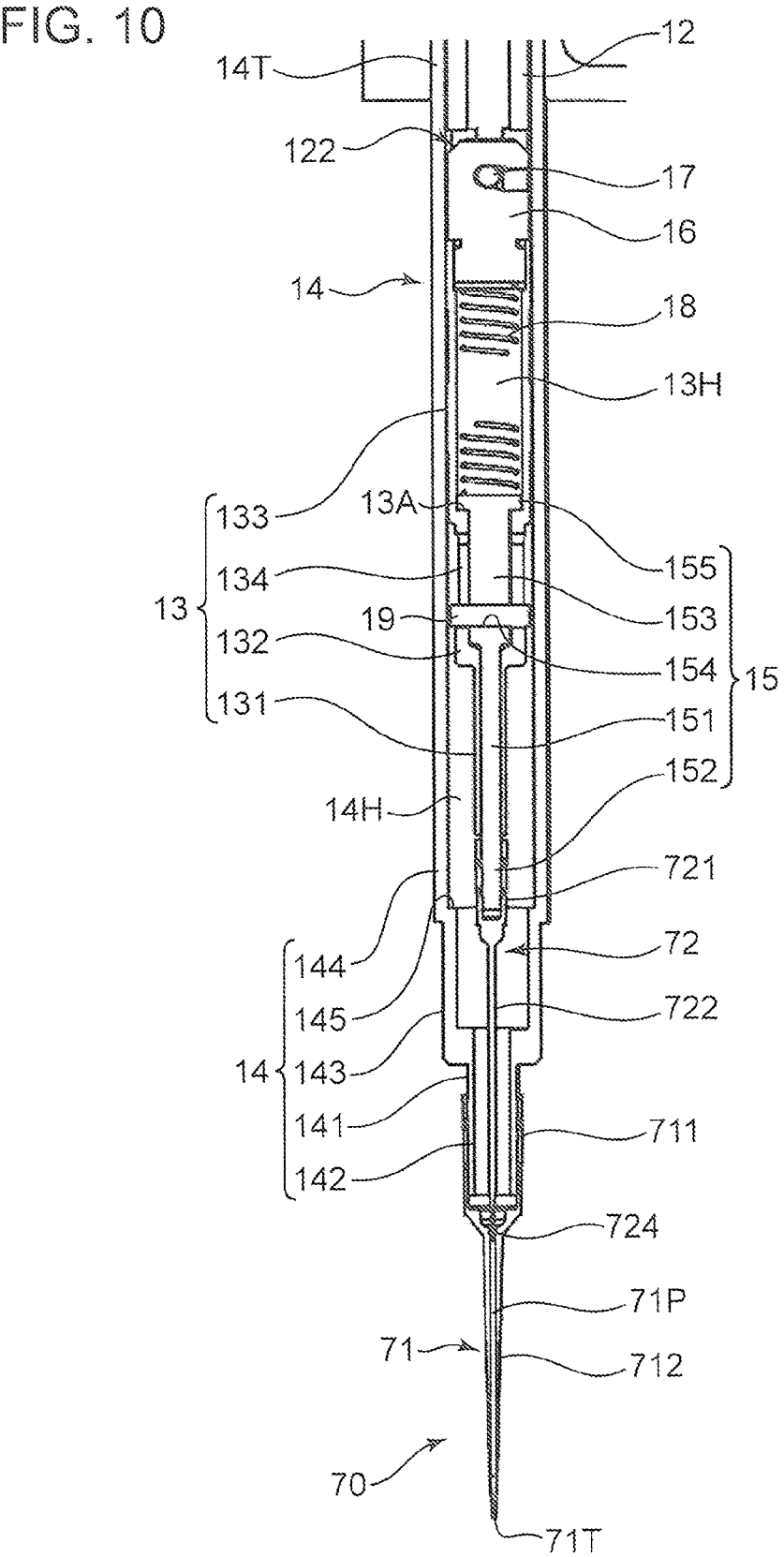
FIG. 10 is a main cross-sectional view of the head in the state in FIG. 9.

Referring also to FIG. 10 as a main cross-sectional view of the head 10, the first cylinder portion 131 of the first cylindrical rod 13 is has an inner diameter slightly larger than the first outer diameter, and houses the first columnar portion 151 therein. The second cylinder portion 132 has an inner diameter slightly larger than the second outer diameter, and houses the second columnar portion 153 therein. The third cylinder portion 133 has an inner diameter slightly larger than the third outer diameter, and houses the third columnar portion 155 therein. The length of the first columnar portion 151 in the up-down direction is larger than the length of the first cylinder portion 131 in the up-down direction. The length of the second columnar portion 153 in the up-down direction is substantially the same as the length of the second cylinder portion 132 in the up-down direction. The third columnar portion 155 is a disk-shaped member sufficiently shorter than the third cylinder portion 133.

The stopper hole 154 is a hole for inserting therethrough the stopper 19 formed of a columnar pin member. The stopper hole 154 is positioned with the long hole 134 in the state in which the discharge rod 15 is housed in the first cylindrical rod 13. The stopper 19 is assembled to the first cylindrical rod 13 and the discharge rod 15 so as to pass through the long hole 134 and the stopper hole 154 that are positioned with each other. The stopper 19 is a member longer than the outer diameter of the second cylinder portion 132. Thus, in the state in which the stopper 19 is inserted into the long hole 134, both end portions of the stopper 19 protrude from an outer circumferential wall of the second cylinder portion 132 to the side.

The long hole 134 allows a relative movement of the stopper 19 in the up-down direction. This means that the movement range of the discharge rod 15 in the up-down direction in the state in which the stopper 19 is inserted through the stopper hole 154, that is, the movement range of the discharge rod 15 relative to the first cylindrical rod 13 is regulated by the range of the length of the long hole 134 in the up-down direction. FIG. 10 illustrates the state in which the stopper 19 is in contact with a lower end of the long hole 134. In this state, a lower end of the first columnar portion 151, that is, the plunger mounting portion 152 protrudes from the first cylinder portion 131.

The coil spring 18 is a spring to be elongated in the up-down direction to generate an urging force. In the cylindrical space 13H in the first cylindrical rod 13, the coil spring 18 is interposed between a lower end surface of the coupler piece 16 and an upper surface of the third columnar portion 155 (between the shaft member 11 and the discharge rod 15). The coupler piece 16 is screwed to the first cylindrical rod 13, and hence the coil spring 18 generates an urging force of pressing the discharge rod 15 downward. Due to the urging force, as illustrated in FIG. 10, a lower surface of the third columnar portion 155 (part of the discharge rod 15) abuts, so as to stop, on a step portion 13A formed on the basis of an inner diameter difference between the second cylinder portion 132 and the third cylinder portion 133 (part of the first cylindrical rod 13). The abutment involving the urging force enables the discharge rod 15 to coordinate with the vertical movement of the second screw shaft 12 (shaft member 11). Note that when the stopper 19 interferes with the locking portion 145 of the second cylindrical rod 14, the discharge rod 15 does not coordinate with the vertical movement, but the coil spring 18 is compressed. This feature is described later.

The second cylindrical rod 14 has a shape whose outer diameter is increased from the lower side to the upper side in three stages. The second cylindrical rod 14 includes a first cylinder portion 141 that is located at the lowest position and has the smallest outer diameter, a second cylinder portion 143 that is continuously provided above the first cylinder portion 141 and has a diameter larger than that of the first cylinder portion 141, and a third cylinder portion 144 that is continuously provided above the second cylinder portion 143 and has a diameter larger than that of the second cylinder portion 143. The second cylindrical rod 14 has a housing space 14H for housing the first cylindrical rod 13 so that the first cylindrical rod 13 is movable in the up-down direction. The inner diameter of the housing space 14H is increased from the lower side to the upper side in accordance with the outer diameters of the first, second, and third cylinder portions 141, 143, and 144. Further, the vicinity of a lower end of the first cylinder portion 141 is a syringe mounting portion 142 onto which the syringe base end portion 711 of the syringe 71 is to be fitted.

An upper end part 14T of the second cylindrical rod 14 is held by the rod holding frame 214 in a fixed manner. Thus, the second cylindrical rod 14 moves in the up-down direction integrally with the first frame 21, but does not move relative to the first frame 21. In other words, the first cylindrical rod 13 coordinates with the second screw shaft 12 and hence moves relative to the first frame 21, but the second cylindrical rod 14 is stationary.

A locking portion 145 to interfere with the stopper 19 is provided in the second cylindrical rod 14. The locking portion 145 is provided on an inner surface at a boundary portion between the second cylinder portion 143 and the third cylinder portion 144, and is a step portion formed on the basis of an inner diameter difference between the second cylinder portion 143 and the third cylinder portion 144. A stopper 19 inserted into the stopper hole 154 in the discharge rod 15 in the horizontal direction has a length shorter than the inner diameter of the third cylinder portion 144 and longer than the inner diameter of the second cylinder portion 143. Thus, when the discharge rod 15 provided with the stopper 19 is lowered to a predetermined position, both ends of the stopper 19 interfere with the locking portion 145.

The mounting head 10 configured as described above operates the cylinder tip 70 to suck and discharge a cell aggregate. Specifically, when the discharge rod 15 coordinates with the movement of the second screw shaft 12 (shaft member 11) in the up-down direction, the plunger 72 mounted to the discharge rod 15 reciprocates in the tubular passage 71P in the syringe 71, thereby sucking a cell aggregate from the suction port 71T into the tubular passage 71P and discharging the sucked cell aggregate from the suction port 71T. This operation is now described with reference to FIG. 9 to FIG. 12.

Figure 9:
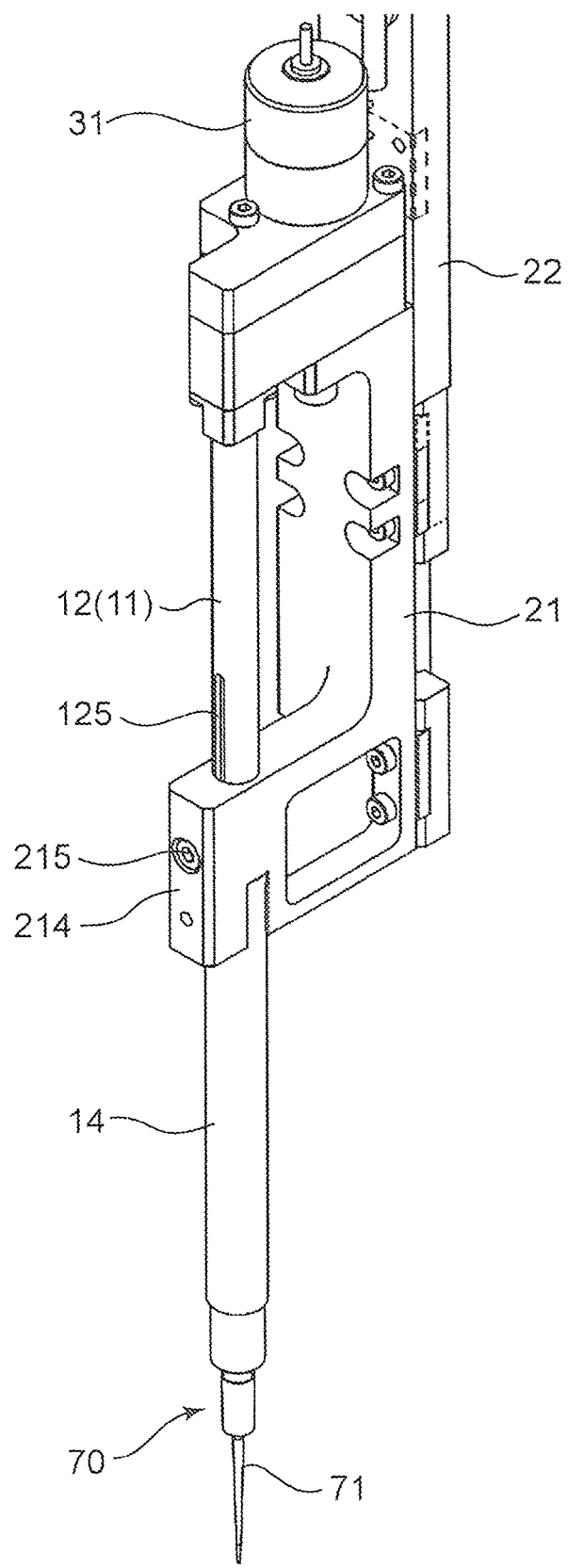
FIG. 9 is a perspective view illustrating a state in which a discharge rod is raised in the head.

FIG. 9 is a perspective view illustrating the state in which the discharge rod 15 is raised in the head 10. FIG. 10 is a main cross-sectional view of the head 10 in the state in FIG. 9. The state in FIG. 9 and FIG. 10 corresponds to the state in which the operation of sucking the cell aggregate is performed in Step 4 (see FIG. 6D). During the suction operation, the first screw shaft 11A is driven to rotate so that the second screw shaft 12 moves upward.

When the second screw shaft 12 rises, the first cylindrical rod 13 that is coupled to the second screw shaft 12 via the coupler piece 16 and the coupler pin 17 also rises integrally therewith. Further, the discharge rod 15 also coordinates with the rise of the second screw shaft 12 because a lower surface of the third columnar portion 155 of the discharge rod 15 abuts, so as to stop, on the step portion 13A of the first cylindrical rod 13 due to the urging force of the coil spring 18. Thus, the plunger 72 having the plunger base end portion 721 fitted into the plunger mounting portion 152 of the discharge rod 15 moves upward relative to the syringe 71 mounted to the stationary second cylindrical rod 14.

FIG. 9 and FIG. 10 illustrate the state in which the second screw shaft 12 moves to the uppermost position in the movable range of the second screw shaft 12. In this state, the guide screw 215 is located in the vicinity of the lower end of the long groove 125 in the second screw shaft 12. The plunger main body portion 722 of the plunger 72 is almost completely separated from the tubular passage 71P in the syringe main body portion 712, and only the vicinity of the distal end portion 724 is inserted into the vicinity of the upper end of the tubular passage 71P. In this manner, a cell aggregate can be sucked into the tubular passage 71P.

Figure 11:
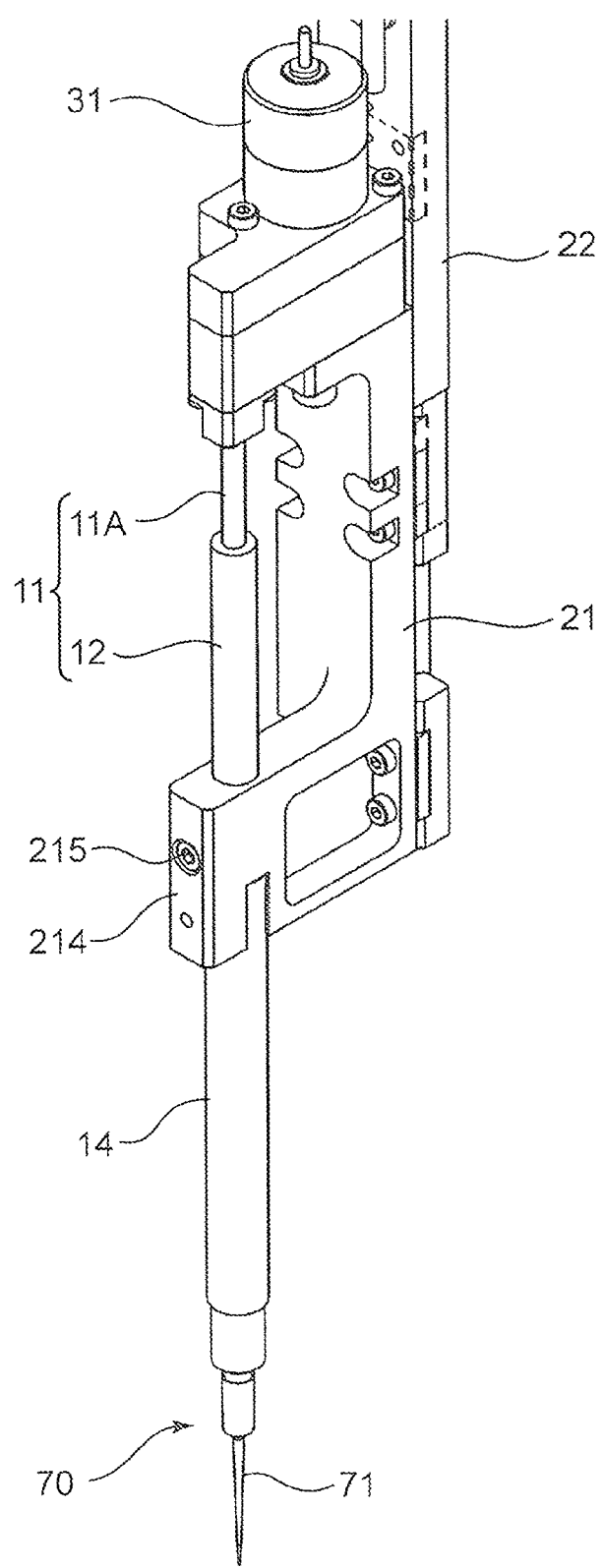
FIG. 11 is a perspective view illustrating a state in which the discharge rod is lowered in the head.
Figure 12:
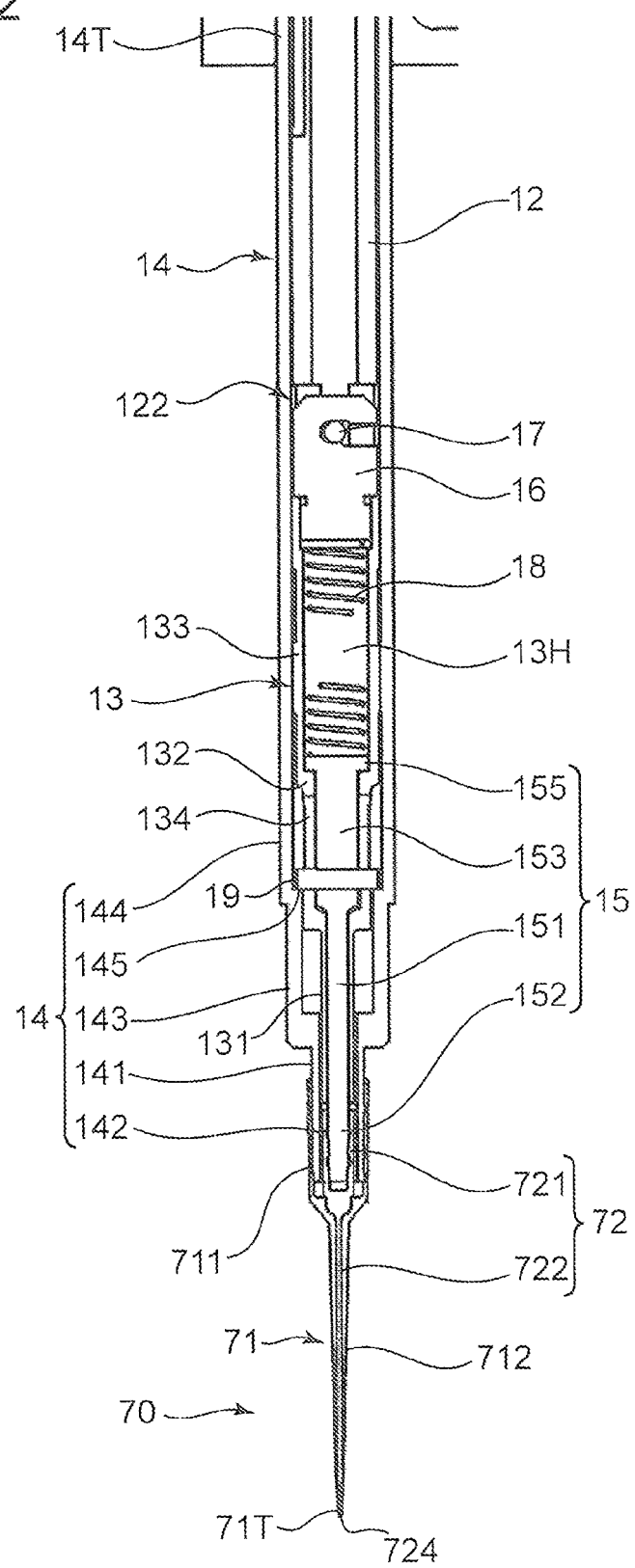
FIG. 12 is a main cross-sectional view of the head in the state in FIG. 11.

FIG. 11 is a perspective view illustrating the state in which the discharge rod 15 is lowered. FIG. 12 is a main cross-sectional view of the head 10 in the state in FIG. 11. The states in FIG. 11 and FIG. 12 correspond to the state before the operation of sucking the cell aggregate in Step 2 is performed (see FIG. 6B) and the state in which the operation of discharging the cell aggregate in Step 5 is performed (see FIG. 6E), respectively. During the operations, the first screw shaft 11A is driven to rotate so that the second screw shaft 12 moves downward.

When the second screw shaft 12 lowers from the state illustrated in FIG. 9 and FIG. 10, the first cylindrical rod 13 coupled to the second screw shaft 12 also lowers integrally. Further, the discharge rod 15 also coordinates with the lowering of the second screw shaft 12 because the third columnar portion 155 and the step portion 13A abut, so as to stop, on each other due to the urging force of the coil spring 18. Accordingly, the plunger 72 mounted to the discharge rod 15 moves downward so as to be inserted into the syringe 71.

FIG. 11 and FIG. 12 illustrate the state in which the second screw shaft 12 moves to the lowest position in the movable range thereof. In this state, the guide screw 215 is located in the vicinity of the upper end of the long groove 125 in the second screw shaft 12. The plunger main body portion 722 of the plunger 72 is inserted into the tubular passage 71P in the syringe main body portion 712 most deeply, and the distal end portion 724 protrudes from the suction port 71T. In this manner, the state in which no air is present in the tubular passage 71P or the state in which a cell aggregate once sucked in the tubular passage 71P is discharged can be formed.

The above-mentioned state is an operating state (referred to as "first state") in which the discharge rod 15 coordinates with the movement of the second screw shaft 12 (shaft member 11) in the up-down direction, thereby sucking and discharging an object to and from the cylinder tip 70. The head 10 in this embodiment can form an operating state (referred to as "second state") for stopping the discharge rod 15 irrespective of the movement of the second screw shaft 12 in the up-down direction. The second state is mainly used to automatically remove the cylinder tip 70 from the head 10. This feature is now described.

Figure 13:
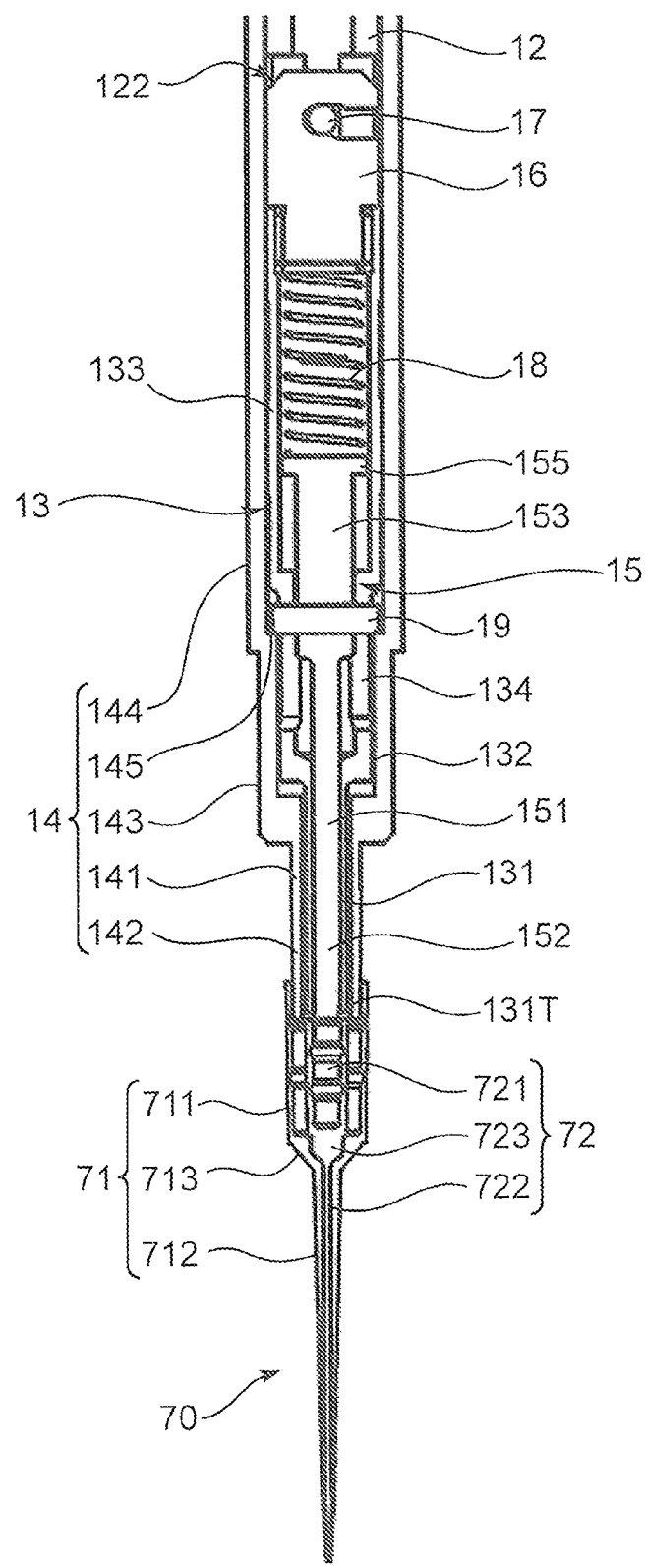
FIG. 13 is a cross-sectional view illustrating a state in which a first cylindrical rod is lowered to remove a cylinder tip.

FIG. 13 is a cross-sectional view illustrating a state in which the first cylindrical rod 13 is lowered more from the state in FIG. 12 so that the cylinder tip 70 is removed. In the first state, the plunger mounting portion 152 of the discharge rod 15 protrudes downward from the lower end (first cylinder portion 131) of the first cylindrical rod 13, and the plunger 72 reciprocates in the tubular passage 71P in the syringe 71 along with the movement of the second screw shaft 12 in the up-down direction. In the second state, on the other hand, the plunger mounting portion 152 is housed in the cylindrical space 13H in the first cylindrical rod 13 along with the movement of the screw shaft 12 in the down direction. In this manner, the upper edge of the plunger 72 (plunger base end portion 721) mounted to the plunger mounting portion 152 is pressed by a lower end 131T of the first cylindrical rod 13 and the plunger 72 is separated from the discharge rod 15. The syringe 71 is also separated from the second cylindrical rod 14 by being pressed by the separating force of the plunger 72.

The operation is now described in detail. When the screw shaft 12 moves downward from the state in FIG. 12 (first state) (when the state shifts to the second state), the first cylindrical rod 13 also moves downward integrally. On the other hand, the discharge rod 15 cannot move downward anymore because the stopper 19 interferes with the locking portion 145 of the second cylindrical rod 14. Specifically, in the first state, due to the urging force of the coil spring 18, the third columnar portion 155 of the discharge rod 15 abuts, so as to stop, on the step portion 13A of the first cylindrical rod 13, and the head 10 operates in the range where the stopper 19 does not interfere with the locking portion 145, and hence the discharge rod 15 coordinates with the vertical movement of the second screw shaft 12. However, when the second state is established, the stopper 19 and the locking portion 145 interfere with each other, and the discharge rod 15 no longer coordinates with the vertical movement of the second screw shaft 12. In this embodiment, the coil spring 18, the stopper 19, and the locking portion 145 form a coordinating mechanism.

In the second state, the stopper 19 and the locking portion 145 interfere with each other so that the discharge rod 15 moves upward relative to the first cylindrical rod 13 against the urging force of the coil spring 18. In other words, the coil spring 18 is compressed. In this case, the stopper 19 moves upward relatively in the long hole 134. Such a moving operation enables the plunger mounting portion 152 of the discharge rod 15 to be gradually housed in the first cylinder portion 131 of the first cylindrical rod 13. Then, the lower end 131T of the first cylindrical rod 13 abuts on an upper edge of the plunger base end portion 721 to push the plunger 72 downward.

FIG. 13 illustrates the state in which the first cylindrical rod 13 is lowered at the lowest position. In this state, the stopper 19 is located at the upper end of the long hole 134, the first cylinder portion 131 completely covers the plunger mounting portion 152, and the lower end 131T is substantially flush with the lower end of the discharge rod 15. Thus, when this state is established, the plunger 72 is separated from the plunger mounting portion 152.

In addition, in this embodiment, when the first cylindrical rod 13 is lowered to the lowest position, the lower end 131T and the lower end of the second cylindrical rod 14 are similarly flush with each other. Specifically, the height position of the plunger mounting portion 152 of the discharge rod 15 housed in the cylindrical space 13H in the first cylindrical rod 13 is substantially the same as the height position of the syringe mounting portion 142 of the second cylindrical rod 14. Thus, when the plunger 72 is pressed by the lower end 131T and separated from the plunger mounting portion 152, the syringe 71 is also pressed by the plunger 72 and separated from the syringe mounting portion 142. This is based on the fact that when the plunger 72 is gradually separated from the plunger mounting portion 152 due to the pressing of the lower end 131T, the hemisphere portion 723 (FIG. 4) presses the tapered cylinder portion 713 of the syringe 71 to gradually separate the syringe 71 from the syringe mounting portion 142. In this manner, according to this embodiment, both the plunger 72 and the syringe 71 can be automatically removed from the head 10 by the operation of moving the second screw shaft 12 in the down direction. Note that this operation corresponds to the operation in Step 6.

Figure 14:
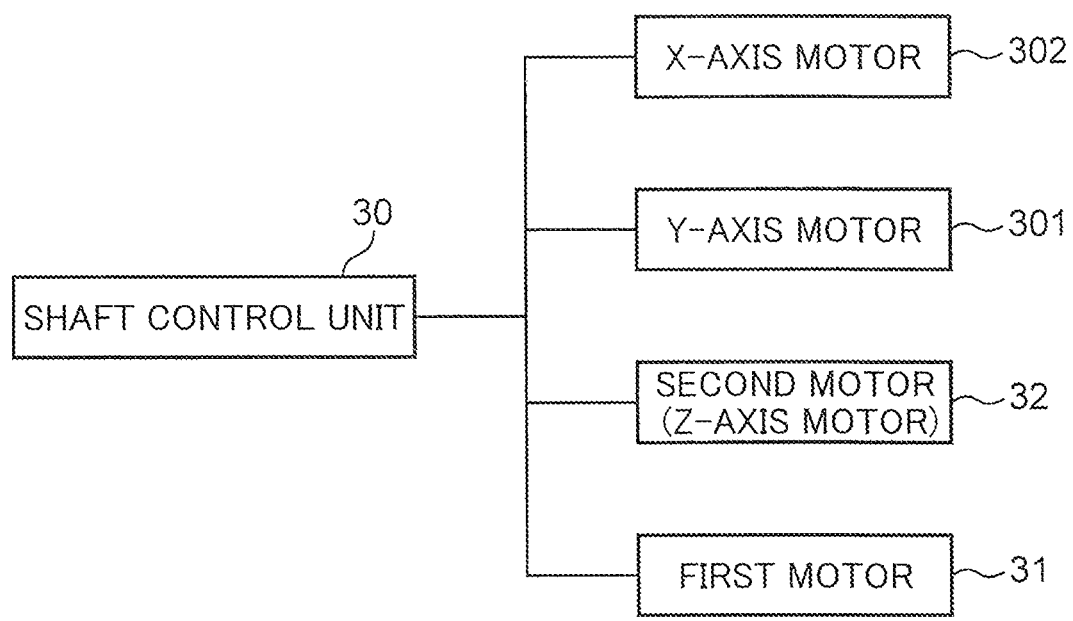
FIG. 14 is a block diagram illustrating a control configuration for the head device.

FIG. 14 is a block diagram illustrating a control configuration of the head device 1. The head device 1 includes a shaft control unit 30 (control unit) in order to control movement of the shaft member 11 (second screw shaft 12) in the up-down direction and control movement of the head device 1 itself in the X direction, Y direction, and Z direction. The shaft control unit 30 controls the first motor 31 and the second motor 32 (Z-axis motor; a mechanism for moving the head 10 as a whole in the up-down direction) and an X-axis motor 302 and a Y-axis motor 301 (a head movement mechanism for moving the head device 1 in the horizontal direction) that are not illustrated in the figures referred to above.

The first motor 31 rotates the first screw shaft 11A to vertically move the second screw shaft 12, thereby sucking and discharging a cell aggregate (object) by using the cylinder tip 70 and separating the cylinder tip 70 from the head 10 as described above. The second motor 32 operates the ball screw device 3A to move the first frame 21 having the head 10 mounted thereto in the Z direction. The X-axis motor 302 is mounted to an X guide frame (not shown) configured to guide the movement of the head device 1 in the X direction, and moves the head device 1 in the X direction. The Y-axis motor 301 is mounted to a Y guide frame (not shown) configured to guide the head device 1 in the Y direction, and moves the head device 1 in the Y direction.

The shaft control unit 30 controls drive of the first motor 31 to control the operation of the second screw shaft 12 in the up-down direction, thereby controlling the operation of sucking and discharging the cell aggregate and further the operation of removing the cylinder tip 70.

Further, the shaft control unit 30 controls drive of the second motor 32 to control the height position of the head 10 in the Z direction. For example, in the operation of lowering the cylinder tip 70 as a whole in Step 3 and Step 5 (see FIG. 6C and FIG. 6E) and the operation of raising the cylinder tip 70 as a whole after the suction in Step 4 (FIG. 6D), the shaft control unit 30 controls the second motor 32 to control the lowering and raising operations.

In addition, the shaft control unit 30 controls drive of the X-axis motor 302 and the Y-axis motor 301 to control the movement of the head device 1 in the X direction and the Y direction. For example, in transition from Step 4 to Step 5, the shaft control unit 30 controls the X-axis motor 302 and the Y-axis motor 301 to move the head device 1 so that the head 10 (cylinder tip 70) moves from above the first container C1 to above the second container C2.

As described above, according to the head 10 in this embodiment, the plunger 72 of the cylinder tip 70 is fitted to the discharge rod 15 configured to coordinate with the movement of the second screw shaft 12 of the shaft member 11 in the up-down direction, and the syringe 71 is fitted into the stationary second cylindrical rod 14. The plunger 72 moves upward relative to the syringe 71 along with the movement of the discharge rod 15 in the up direction, and a cell aggregate as an object is sucked into the tubular passage 71P in the syringe 71. After that, the object sucked into the tubular passage 71P is discharged from the cylinder tip 70 along with the movement of the discharge rod 15 in the down direction. Consequently, simply by moving the second screw shaft 12 in the up-down direction, the suction of the object into the cylinder tip 70 and the discharge of the object from the cylinder tip 70 can be executed.

Further, according to the head 10 in this embodiment, in the first state, the discharge rod 15 coordinates with the movement of the second screw shaft 12 in the up-down direction, and hence the suction into the cylinder tip 70 and the discharge therefrom can be executed by the vertical movement of the second screw shaft 12. In the second state, on the other hand, the discharge rod 15 does not coordinate with the movement of the second screw shaft 12 in the up-down direction, and when the second screw shaft 12 moves downward, only the first cylindrical rod 13 is lowered so that the discharge rod 15 is housed in the cylindrical space 13H. In this case, the plunger 72 mounted to the plunger mounting portion 152 is pressed by the lower end 131T of the first cylindrical rod 13 and separated from the plunger mounting portion 152. Further, the syringe 71 can also be separated from the syringe mounting portion 142 along with the separation of the plunger 72. Consequently, the cylinder tip 70 can be automatically removed from the head 10 by the operation of moving the second screw shaft 12 in the down direction.

Figure 15:
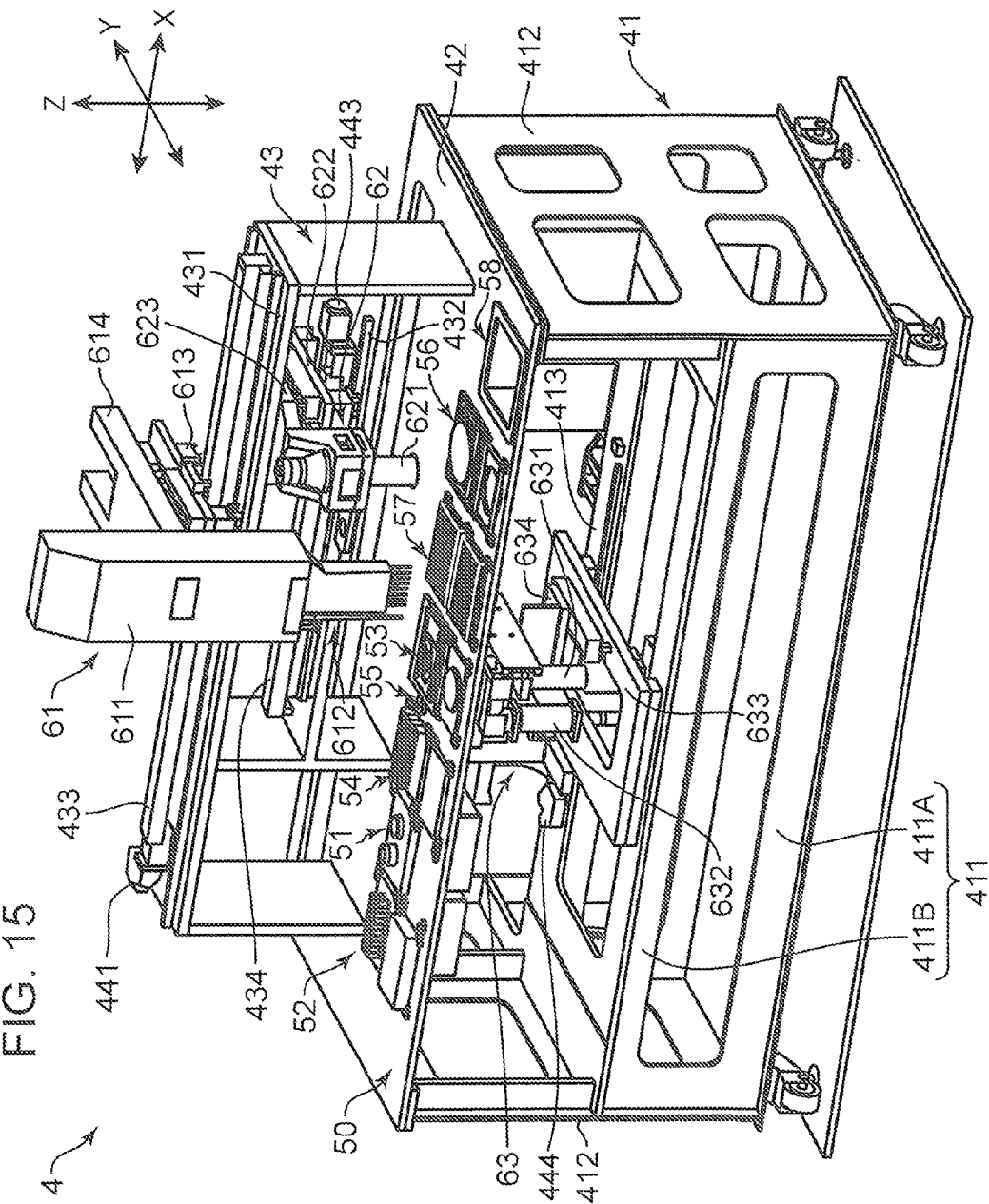
FIG. 15 is a perspective view of a cell moving device to which the head device is applied.
Figure 16:
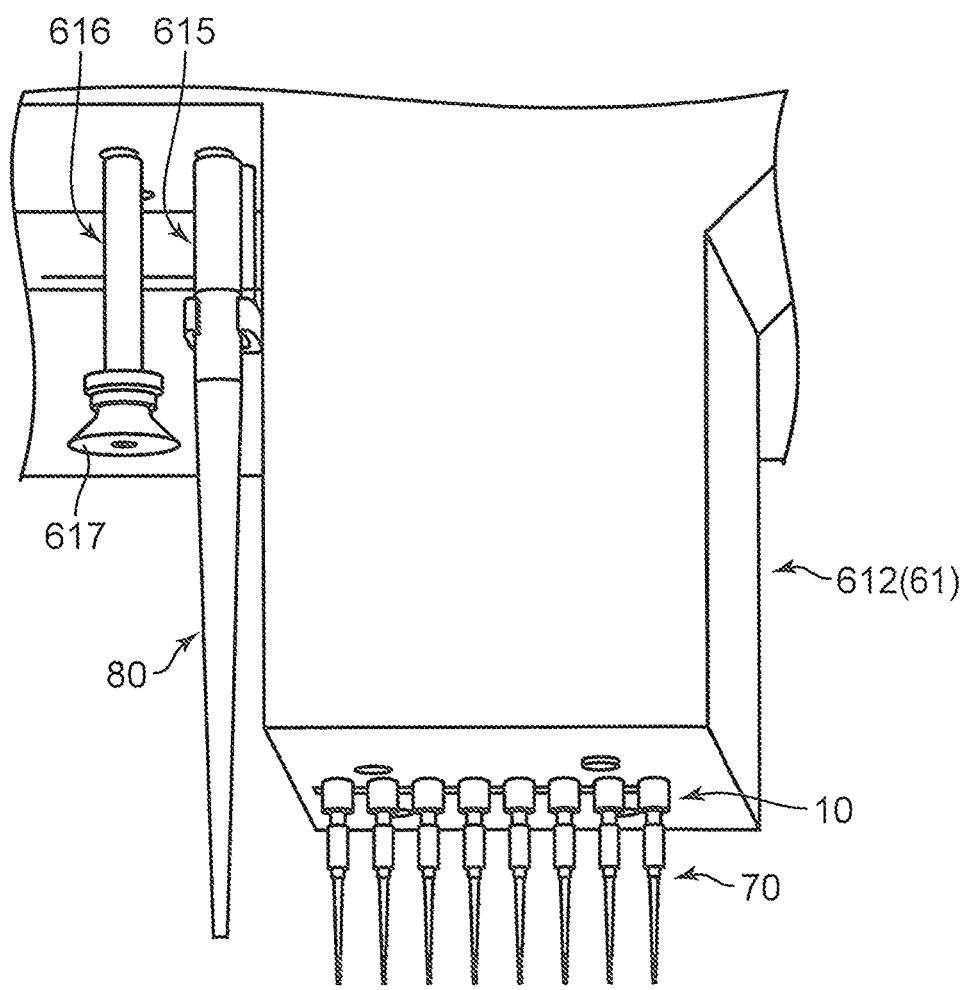
FIG. 16 is a perspective view of a head unit.

Subsequently, a cell moving device 4 to which the head 10 and the head device 1 according to this embodiment are suitably applied is exemplified. FIG. 15 is a perspective view of the movement device 4. FIG. 16 is a perspective view of a head unit 61 in which the head 10 (head device 1) is assembled. The movement device 4 includes a support frame 41, a base 42 supported by the support frame 41, a cell movement line 50 assembled to the base 42, a head unit 61 and an illumination unit 62 that are arranged above the base 42, and an imaging unit 63 arranged below the base 42.

The support frame 41 includes a base frame 411 and a pair of side frames 412. The base frame 411 is a rectangular parallelepiped-shaped frame assembly elongated in the X direction. The base frame 411 includes a rectangular lower layer frame 411A and an upper layer frame 411B provided above the lower layer frame 411A. A guide rail 413 for moving the imaging unit 63 in the X direction is provided on an upper surface of the upper layer frame 411B. The base 42 is a rectangular flat plate which has a predetermined rigidity, which is formed of a translucent material in part or in its entirety, and which has substantially the same size as the base frame 411 in top view.

A frame stand 43 is vertically arranged on the base 42. The frame stand 43 includes an upper frame 431 and an intermediate frame 432 that are flat plates extending in the X direction. An upper guide rail 433 for moving the head unit 61 along the X direction is assembled to an upper surface of the upper frame 431. Further, an intermediate guide rail 434 for moving the illumination unit 62 along the X direction is assembled to an upper surface of the intermediate frame 432.

The cell movement line 50 is formed such that elements necessary for implementation of a series of cell movement steps of extracting a desired cell aggregate from a cell-containing liquid and moving the extracted cell aggregate to a predetermined container are arranged in the X direction. The cell movement line 50 includes an object stock portion 51 configured to store a cell-containing liquid, a dispenser tip stock portion 52, a cell sorting portion 53 to which the cell-containing liquid is poured and which is configured to sort cell aggregates, a tip stock portion 54, a tip imaging portion 55, a cell transfer portion 56 configured to receive a sorted cell aggregate, a black cover placement portion 57, and a tip discarding portion 58. In this case, the cell sorting portion 53 is a container corresponding to the first container C1 illustrated in FIGS. 6A to 6D, and the cell transfer portion 56 is a container corresponding to the second container C2 illustrated in FIG. 6E.

The head unit 61 includes a unit main body 611, a head portion 612, an X slider 613, and a Y slider 614. As illustrated in FIG. 16, the head portion 612 includes a plurality of the heads 10 described above, a first nozzle 615, and a second nozzle 616. This embodiment indicates an example in which eight heads 10 are arranged in line in the X direction. The number of the heads 10 is freely selected, and the heads 10 may be arranged in a matrix in the X-Y direction. The first nozzle 615 and the second nozzle 616 with a sucking disk 617 are assembled to the unit main body 611 so as to be vertically movable. A piston mechanism for generating a suction force and a discharge force is provided inside each of the first nozzle 615 and the second nozzle 616. A mechanism for moving the head 10 in the Z direction, such as the ball screw device 3A illustrated in FIG. 1 to FIG. 3, is built in the unit main body 611.

The X slider 613 is assembled to the upper guide rail 433. An X drive motor 441 corresponding to the X-axis motor 302 in FIG. 14 is attached to the upper guide rail 433. When the X drive motor 441 operates, the X slider 613 moves on the upper guide rail 433 in the X direction. The Y slider 614 supports the unit main body 611 at one end (front end) in the Y direction. The Y slider 614 is assembled to a Y rail (not shown in FIG. 15) arranged on an upper surface of the X slider 613. When a drive motor (not shown) (corresponding to the Y-axis motor 301 in FIG. 14) attached to the Y rail operates, the Y slider 614 and the unit main body 611 move in the Y direction. Specifically, when the unit main body 611 moves along the upper guide rail 433 and the Y rail, the head portion 612 is freely movable in the X direction and the Y direction. Thus, the head portion 612 can move, above the base 42, along a predetermined path on the cell movement line 50.

The illumination unit 62 is arranged above the base 42 so as to be movable in order to illuminate mainly the cell sorting portion 53 and the cell transfer portion 56 from above. The illumination is used as transmitted illumination for imaging a cell aggregate held in the cell sorting portion 53 or the cell transfer portion 56 with the imaging unit 63. The illumination unit 62 includes an illumination device 621 configured to emit illumination light, an X slider 622, and a holder 623. The X slider 622 is assembled to the intermediate guide rail 434. An illumination unit drive motor 443 is attached to the intermediate guide rail 434. When the drive motor 443 operates, the X slider 622 moves on the intermediate guide rail 434 in the X direction. A holder 623 holds the illumination device 621, and is assembled to the X slider 622 so as to be movable for a short distance in the Y direction by a drive device (not shown). Thus, the illumination device 621 is movable above the base 42 in the X direction and the Y direction.

The imaging unit 63 is arranged below the base 42 so as to be movable in order to image cell aggregates held in the cell sorting portion 53 and the cell transfer portion 56 from below the base 42. In this embodiment, the imaging unit 63 is also used to observe how the cylinder tip 70 is mounted to the head 10 in the tip imaging portion 55. The imaging unit 63 includes a camera 631, an epi-illumination device 632, an X slider 633, and a holder 634.

The camera 631 includes a CCD image sensor and an optical system configured to form an optical image on a light receiving surface of the CCD image sensor. The epi-illumination device 632 is a light source used when an object to be imaged by the camera 631 is not a light transmissive member or is fluorescently stained. The X slider 633 is assembled to the guide rail 413 of the support frame 41. An imaging unit drive motor 444 is attached to the guide rail 413. When the drive motor 444 operates, the X slider 633 moves on the guide rail 413 in the X direction. A holder 634 holds the camera 631 and the epi-illumination device 632, and is assembled the X slider 633 so as to be movable for a short distance in the Y direction by a drive device (not shown). Thus, the camera 631 is movable below the base 42 in the X direction and the Y direction.

FIG. 17 is a perspective view of the cell movement line 50, with the illustration of the base 42 omitted and the components of the cell movement line extracted. In FIG. 17, the arrangement positions of the head unit 61, the illumination unit 62, and the imaging unit 63 are schematically indicated. In the cell movement line 50, the dispenser tip stock portion 52, the object stock portion 51, the tip stock portion 54, the tip imaging portion 55, the cell sorting portion 53, the black cover placement portion 57, the cell transfer portion 56, and the tip discarding portion 58 are arranged in line in this order from the upstream side in the X direction (left end side in FIG. 17). The position of each of the portions on the base 42 is determined by positioning members 42S. The arrangement in the cell movement line 50 illustrated in FIG. 17 is merely an example and the arrangement positions of the portions can be appropriately set in consideration of work efficiency and the like. For example, the black cover placement portion 57 may be arranged on the front side (+Y) or the back side (−Y) of the cell sorting portion 53 and the cell transfer portion 56.

The object stock portion 51 is a site where a cell culture liquid (liquid) dispersed with a large amount of cell aggregates (objects) as a dispensing source is stored. The object stock portion 51 includes a box 511 arranged at a predetermined position on the base 42, a tube 512 held in the box 511, and a lid member 513 placed on the box 511. The tube 512 is a cylindrical container whose upper surface is opened, and stores a cell culture liquid containing cell aggregates and impurities. The lid member 513 is a member for closing the opening in the tube 512.

The dispenser tip stock portion 52 is a site where a plurality of dispenser tips 80 are stored. The dispenser tip 80 is an elongated tube-shaped member, and includes an upper end portion to be fitted into the first nozzle 615, and a lower end portion that has an opening formed at an edge thereof for sucking and discharging a cell culture liquid. The dispenser tip 80 is mountable and removable to and from the first nozzle 615. The dispenser tip 80 sucks a cell culture liquid when the suction force is applied from the first nozzle 615, and discharges the sucked cell culture liquid when the discharge force is applied. The dispenser tip stock portion 52 includes a holding box 521 configured to hold the dispenser tips 80 that are arranged in a matrix in a standing manner, and a box lid member 523. A holder member 522 for holding the dispenser tips 80 in an aligned manner is arranged in the holding box 521.

The cell sorting portion 53 is a site for sorting a desired size of a cell aggregate from a cell culture liquid containing various sizes of cell aggregates and impurities. The cell sorting portion 53 includes a dish 64, a holding table 531, and a table lid member 532. The dish 64 is an upper surface-opened container into which a cell culture liquid containing cell aggregates is poured by the dispenser tip 80 and which is capable of storing the cell culture liquid. The holding table 531 holds the dish 64 in a positioned manner. The table lid member 532 is a lid member for covering the dish 64 and the upper surface of the holding table 531.

The dish 64 includes a well plate that has, on the upper surface side, a plurality of recesses for carrying cell aggregates. A through hole is provided in a bottom part of the recess. The cell aggregate to be extracted is held by the recess, and impurities and the like drop through the through hole. Sorting of the cell aggregate and impurities is implemented as described above, and hence only the cell aggregate is left on the well plate. An image of the cell aggregate carried in the recess is taken by the camera 631 under illumination of the illumination unit 62. In this manner, the position of the cell aggregate to be sucked is specified.

The tip stock portion 54 is a site where a large number of the cylinder tips 70 are held. The cylinder tip 70 is mountable and removable to and from the head 10. The cylinder tip 70 functions to suck a cell aggregate carried in the recess of the well plate, transport the cell aggregate along with the movement of the head unit 61, and discharge the cell aggregate to the cell transfer portion 56.

The tip stock portion 54 includes a holding box 541 and a box lid member 543. The holding box 541 holds the cylinder tips 70 that are arranged in a matrix in a standing manner. A holder member 542 for holding the cylinder tips 70 in an aligned manner is arranged in the holding box 541. The cylinder tip 70 is held in the holding box 541 in a state in which an upper end part of the cylinder tip 70 protrudes upward from an upper end surface of the holding box 541. Specifically, the cylinder tip 70 is held in the holding box 541 in a state in which the cylinder tip 70 is easily mountable to the head 10 moving in the Z direction. The box lid member 543 is a lid member to be put on an upper end surface of the holding box 541, for covering the cylinder tip 70.

The tip imaging portion 55 is a pit for providing a position at which an image of the cylinder tip 70 mounted to the head 10 is taken. The imaging is performed by the imaging unit 63. For the imaging, the camera 631 of the imaging unit 63 is moved directly below the tip imaging portion 55, and takes an image of each cylinder tip 70 under illumination of the epi-illumination device 632. XYZ coordinate positions of the suction port 71T in the cylinder tip 70 are determined on the basis of the image of the cylinder tip 70 and focus positional information at the time of the imaging. A correction value is derived on the basis of a difference between the coordinate positions and predetermined reference positions. The correction value is used as a correction value for movement control of the head 10. Note that, instead of the epi-illumination device 632, an illumination device such as an LED illumination device may be installed in the tip imaging portion 55 itself so that the imaging is performed under illumination of the illumination device.

The cell transfer portion 56 is arranged in the vicinity of the downstream-side end portion of the cell movement line 50 in the X direction, and is a site as a movement destination of the cell aggregate sucked from the dish 64 in the cell sorting portion 53. The cell transfer portion 56 includes a microplate 65, a holding table 561, and a table lid member 562. Note that a container similar to the dish 64 may be provided on the cell transfer portion 56 instead of the microplate 65.

The microplate 65 is a plate in which a large number of small wells 66 with upper surfaces opened are arranged in a matrix. The microplate 65 is formed of a translucent member, such as transparent plastic. In general, one cell aggregate is housed in one well 66. Thus, a cell aggregate housed in each well 66 can be imaged by the camera 631. Further, the arrangement pitch of the wells 66 is set to substantially the same as the arrangement pitch of a group of cylinder tips 70 mounted to the heads 10 arranged in line. Consequently, cell aggregates can be discharged to the wells 66 concurrently from a group of the cylinder tips 70. Note that a designated number of cell aggregates may be housed in one well 66, or a designated amount (total volume or total area) of cell aggregates may be housed in one well 66. The holding table 561 holds the microplate 65 in a positioned manner. The table lid member 562 is a lid member for covering the microplate 65 and the upper surface of the holding table 561.

The black cover placement portion 57 is a site where a first black cover 571 to be put on the cell transfer portion 56 and a second black cover 572 to be put on the cell sorting portion 53 are placed. The first and second black covers 571 and 572 are light shielding members used to image a cell aggregate carried on the dish 64 or the microplate 65 in a light shielded state. The first and second black covers 571 and 572 are put on the holding tables 531 and 561 so as to cover the holding tables 531 and 561, for example, when a fluorescent agent is added to the cell culture liquid for fluorescent observation of the cell aggregate.

The tip discarding portion 58 is a site arranged on the most downstream-side end portion in the cell movement line 50 in the X direction, where the used cylinder tip 70 and dispenser tip 80 that have finished the suction and discharge operation are discarded. The tip discarding portion 58 includes a collection box 581 for housing the used cylinder tip 70 and dispenser tip 80. For discarding the used tip, the head unit 61 having the cylinder tip 70 or the dispenser tip 80 mounted thereto is moved above an opening portion 582 in the collection box 581, and the operation of removing the cylinder tip 70 or the dispenser tip 80 from the head portion 612 is executed. With the removal operation, the cylinder tip 70 or the dispenser tip 80 drops in the collection box 581 through the opening portion 582.

The operation of the movement device 4 configured as described above is controlled by a control unit (such as a personal computer connected to the movement device 4) corresponding to the shaft control unit 30 in FIG. 14. The control unit controls the movement device 4 to execute roughly a dispensing operation and a cell movement operation that uses the head 10 according to this embodiment. First, in the dispensing operation, the control unit controls the movement device 4 to successively execute:

(Control 1) Control of moving the head unit 61 above the dispenser tip stock portion 52 and mounting the dispenser tip 80 to the first nozzle 615;

(Control 2) Control of moving the head unit 61 above the object stock portion 51 and sucking a predetermined dispensing amount of a cell culture liquid containing cell aggregates, which is stored in the tube 512, into the dispenser tip 80;

(Control 3) Control of moving the head unit 61 above the cell sorting portion 53 and discharging the cell culture liquid in the dispenser tip 80 into the dish 64; and (Control 4) Control of moving the head unit 61 above the tip discarding portion 58, removing the used dispenser tip 80 from the first nozzle 615, and discarding the used dispenser tip 80 in the collection box 581.

In the cell movement operation, the control unit controls the movement device 4 to successively execute:

(Control 5) Control of moving the head unit 61 above the tip stock portion 54 and mounting the cylinder tip 70 to the head 10;

(Control 6) Control of moving the head unit 61 above the cell sorting portion 53 and sucking the cell aggregate stored in the dish 64 into the cylinder tip 70;

(Control 7) Control of moving the head unit 61 above the cell transfer portion 56 and discharging the cell aggregate in the cylinder tip 70 into the microplate 65; and (Control 8) Control of moving the head unit 61 above the tip discarding portion 58, removing the used cylinder tip 70 from the head 10, and discarding the used cylinder tip 70 into the collection box 581.

Control 5 is control performed before Step 1 in FIG. 6A referred to above. In the movement device 4 in this embodiment, the operation of mounting the cylinder tip 70 to the head 10 is also automated. After the head unit 61 is moved above the tip stock portion 54, one head 10 positioned with one cylinder tip 70 is lowered. In this case, as illustrated in FIG. 4, the lower end surface of the discharge rod 15 and the lower end surface of the second cylindrical rod 14 are set to be substantially flush with each other, but the lower end surface of the first cylindrical rod 13 sinks upward with respect to those lower end surfaces. The sink length is the length by which the plunger mounting portion 152 of the discharge rod 15 is exposed (depth of the mounting hole 72H). When the head 10 in this state is lowered, the plunger mounting portion 152 is press-fitted into the mounting hole 72H in the plunger base end portion 721, and the syringe mounting portion 142 of the second cylindrical rod 14 is press-fitted into the hollow portion 71H in the syringe base end portion 711. In this manner, the mounting of the cylinder tip 70 to the head 10 is completed.

After the mounting, the head unit 61 is moved to the tip imaging portion 55, and the cylinder tip 70 mounted to the head 10 is imaged. Through the imaging, the mounting state of each cylinder tip 70 to the head 10 is detected to determine XYZ coordinate positions of the suction port 71T of the cylinder tip 70 (correction value for XYZ coordinates of the distal end of the head 10).

Control 6 is control for performing the operations of Steps 1 to 4 illustrated in FIG. 6A to FIG. 6D. The operation of sucking a cell aggregate into the cylinder tip 70 is achieved by moving the discharge rod 15 from the lowering state (FIG. 12) to the rising state (FIG. 10) by the drive of the shaft member 11. This feature is as described above.

Control 7 is control for performing the operation of Step 5 illustrated in FIG. 6E. The operation of discharging the cell aggregate in the cylinder tip 70 into the microplate 65 is achieved by changing the rising state of the discharge rod 15 (FIG. 10) to the lowering state (FIG. 12) by the drive of the shaft member 11 in contrast to Control 6.

Control 8 is control for performing the operation of Step 6. The operation of removing the used cylinder tip 70 from the head 10 is achieved by lowering the first cylindrical rod 13 to the lowest position as described above with reference to FIG. 13.

According to the movement device 4 described above, through the application of the head 10 (head device 1) according to the embodiment of the present disclosure, a series of works including the mounting of the cylinder tip 70 to the head 10, the suction of a cell aggregate from the dish 64 (first container C1) with use of the cylinder tip 70, the discharge of the cell aggregate into the microplate 65 (second container C2), and the discarding of the cylinder tip 70 into the tip discarding portion 58 can be automated under control of the control unit. Consequently, the movement work efficiency for a cell aggregate can be remarkably enhanced.

Note that the above-mentioned specific embodiments mainly include the disclosure having the following configurations.

A cylinder tip mounting head according to one aspect of the present disclosure is to be mounted with a cylinder tip, the cylinder tip including: a syringe including a tubular passage inside serving as a suction path for an object; and a plunger configured to reciprocate in the tubular passage, and includes: a shaft member configured to move in an up-down direction; a first cylindrical rod, which is mounted to a lower end of the shaft member, which is configured to move in the up-down direction integrally with the shaft member, and which has a cylindrical space formed therein; a stationary second cylindrical rod, which has a housing space for housing the first cylindrical rod so that the first cylindrical rod is movable in the up-down direction, the stationary second cylindrical rod including, at a lower end, a syringe mounting portion to which a base end portion of the syringe is to be fitted; and a discharge rod housed in the cylindrical space in the first cylindrical rod, the discharge rod including, at a lower end, a plunger mounting portion to which a base end portion of the plunger is to be fitted, in which the discharge rod is configured to coordinate with the movement of the shaft member in the up-down direction so that the plunger mounted to the discharge rod reciprocates in the tubular passage in the syringe to suck the object into the tubular passage and discharge the sucked object.

According to the head, the base end portion of the plunger is fitted to the discharge rod configured to coordinate with the movement of the shaft member in the up-down direction, and the base end portion of the syringe is fitted to the stationary second cylindrical rod. When the discharge rod moves in the up direction, the plunger moves upward relative to the syringe, and the object is sucked into the cylinder tip (into the tubular passage). After that, when the discharge rod moves in the down direction, the object sucked into the tubular passage is discharged from the cylinder tip. Consequently, simply by moving the shaft member in the up-down direction, the suction of the object into the cylinder tip and the discharge of the object from the cylinder tip can be executed.

In the cylinder tip mounting head, it is desired that: the discharge rod be housed in the cylindrical space so as to be movable relative to the first cylindrical rod; the cylinder tip mounting head further includes a coordinating mechanism for forming a first state in which the discharge rod coordinates with the movement of the shaft member in the up-down direction and a second state in which the discharge rod is stopped irrespective of the movement of the shaft member in the up-down direction; in the first state, the plunger mounting portion of the discharge rod protrudes downward from a lower end of the first cylindrical rod, and the plunger reciprocates in the tubular passage along with the movement of the shaft member in the up-down direction; and in the second state, along with movement of the shaft member in a down direction, the plunger mounting portion of the discharge rod is housed in the cylindrical space in the first cylindrical rod, and the plunger mounted to the plunger mounting portion is pressed by the lower end of the first cylindrical rod and separated from the plunger mounting portion.

According to the head, in the first state, the discharge rod coordinates with the movement of the shaft member in the up-down direction, and hence the suction of the object into the cylinder tip and the discharge of the object from the cylinder tip can be executed by the vertical movement of the shaft member. In the second state, on the other hand, the discharge rod does not coordinate with the movement of the shaft member in the up-down direction, and when the shaft member moves downward, only the first cylindrical rod is lowered so that the discharge rod is housed in the cylindrical space. In this case, the plunger mounted to the plunger mounting portion is pressed by the lower end of the first cylindrical rod and separated from the plunger mounting portion. Consequently, the plunger can be automatically removed from the plunger mounting portion by the operation of moving the shaft member in the down direction.

In the cylinder tip mounting head: the coordinating mechanism may include: an elastic member, which is interposed between the shaft member and the discharge rod in the cylindrical space and is configured to generate an urging force; a stopper provided on the discharge rod; and a locking portion, which is provided on the second cylindrical rod and is to interfere with the stopper; in the first state, a part of the discharge rod may abut, so as to stop, on a part of the first cylindrical rod by the urging force, thereby forming a state in which the discharge rod coordinates with the shaft member; and in the second state, the stopper and the locking portion may interfere with each other so that the discharge rod moves upward relatively against the urging force, thereby housing the plunger mounting portion into the cylindrical space.

According to the head, a simple configuration of the elastic member, the stopper, and the locking portion can be used to achieve a mechanism in which the discharge rod coordinates with the vertical movement of the shaft member in the first state and the discharge rod does not coordinate with the vertical movement of the shaft member but is housed in the cylindrical space in the second state.

In the cylinder tip mounting head: the discharge rod may include: a first columnar portion including the plunger mounting portion and having a first outer diameter; a second columnar portion, which is continuously provided above the first columnar portion and has a second outer diameter larger than the first outer diameter, the second columnar portion having the stopper formed therein; and a third columnar portion, which is continuously provided above the second columnar portion and has a third outer diameter larger than the second outer diameter; the first cylindrical rod may include: a first cylinder portion, which has an inner diameter slightly larger than the first outer diameter and is configured to house the first columnar portion; a second cylinder portion, which is continuously provided above the first cylinder portion, has an inner diameter slightly larger than the second outer diameter, and is configured to house the second columnar portion; a third cylinder portion, which is continuously provided above the second cylinder portion, has an inner diameter slightly larger than the third outer diameter, and is configured to house the third columnar portion; and a long hole extending in the up-down direction, which is formed in a circumferential wall of the second cylinder portion and allows relative movement of the stopper; the elastic member may be a coil spring arranged between a lower end surface of the shaft member and an upper surface of the third columnar portion; in the first state, the third columnar portion may abut, so as to stop, on a step based on a diameter difference between the second cylinder portion and the third cylinder portion and be stopped; and in the second state, the stopper may move relatively in the long hole, and a lower end surface of the first cylinder portion may press the base end portion of the plunger.

According to the head, the first state and the second state can be easily and reliably achieved by the discharge rod and the first cylindrical rod, which have simple shapes.

In the cylinder tip mounting head, it is desired that: in the second state, a height position of the plunger mounting portion of the discharge rod housed in the cylindrical space in the first cylindrical rod is substantially the same as a height position of the syringe mounting portion of the second cylindrical rod; and when the plunger mounted to the plunger mounting portion is pressed by the lower end of the first cylindrical rod and separated from the plunger mounting portion, the syringe mounted to the syringe mounting portion is pressed by the plunger and separated from the syringe mounting portion.

According to the head, the height position of the plunger mounting portion of the discharge rod is substantially the same as the height position of the syringe mounting portion of the second cylindrical rod. Thus, when the plunger is separated from the plunger mounting portion, the syringe is also separated from the syringe mounting portion by being pressed by the plunger. Consequently, both the plunger and the syringe can be automatically removed by the operation of moving the shaft member in the down direction.

In the cylinder tip mounting head, it is desired that the shaft member be a screw shaft, and include: a first screw shaft to be applied a rotary drive force; and a second screw shaft including an upper end portion to be screwed with the first screw shaft and a lower end portion to be mounted with the first cylindrical rod.

According to this head, the vertical movement of the shaft member can be achieved by vertical movement of the second screw shaft caused by rotation of the first screw shaft about its axis, and hence a drive system for the shaft member can be simplified.

A head device according to another aspect of the present disclosure includes: the cylinder tip mounting head; a motor configured to generate the rotary drive force; a transmission mechanism configured to transmit the rotary drive force to the shaft member; a frame member configured to hold the motor, the transmission mechanism, and the second cylindrical rod; and a control unit configured to control drive of the motor to control the movement of the shaft member in the up-down direction.

A movement device according to still another aspect of the present disclosure includes: the head device including a mechanism configured to move the cylinder tip mounting head in an up-down direction as a whole; a first container configured to store an object; a second container configured to receive the object; and a head moving mechanism configured to move the head device in a horizontal direction between the first container and the second container.

According to the present disclosure described above, suction of an object with use of the cylinder tip, discharge of the sucked object, and mounting and removal of the cylinder tip to and from the head are automated. Consequently, work efficiency of the object movement work with use of the cylinder tip including the syringe and the plunger can be remarkably improved.

The invention claimed is:

1. A head device which carries out operations to suck an object and discharge the sucked object by using a tip including a suction port, comprising:
   a mounting head which has a cylindrical rod with a lower end including a tip mounting portion to which the tip is to be fitted, and a shaft member equipped in a housing space of the cylindrical rod in a movable manner in an up-down direction and configured to generate a suction force and a discharge force at the suction port by the movement thereof in the up-down direction;
   a first motor configured to generate a drive force for moving the shaft member in the up-down direction;
   a frame member which holds the mounting head and the first motor, the frame member including a coupling portion that receives a moving force;
   a frame moving mechanism including a driving shaft member which is coupled to the coupling portion and a second motor that moves the frame member in the up-down direction by providing a drive force to the driving shaft member; and
   a control unit which controls movement of the shaft member in the up-down direction by controlling drive of the first motor and height position of the head by controlling drive of the second motor.

2. The head device according to claim 1, wherein
   the tip is a cylinder tip which has a syringe including a tubular passage inside serving as a suction path for the object;
   the shaft member includes a first cylindrical rod, which is mounted to a lowest portion of the shaft member;
   the cylindrical rod includes a stationary second cylindrical rod, which has a housing space for housing the first cylindrical rod so that the first cylindrical rod is movable in the up-down direction, and a syringe mounting portion that is a lower portion of the cylindrical rod, serving as the tip mounting portion, to which a base end portion of the syringe is to be fitted; and the control unit moves the shaft member including the first cylindrical rod in the up-down direction to suck the object into the tubular passage and discharge the sucked object.

3. The head device according to claim 1, wherein the tip is a cylinder tip which has a syringe including a tubular passage inside serving as a suction path for the object serving as a suction path for an object, and a plunger configured to reciprocate in the tubular passage;

the shaft member includes a first cylindrical rod, which is mounted to a lowest portion of the shaft member, and which has a cylindrical space formed therein;

the cylindrical rod includes a stationary second cylindrical rod, which has a housing space for housing the first cylindrical rod so that the first cylindrical rod is movable in the up-down direction, and a syringe mounting portion, which is a lower portion of the cylindrical rod, serving as the tip mounting portion, to which a base end portion of the syringe is to be fitted;

the mounting head further includes a discharge rod housed in the cylindrical space in the first cylindrical rod, the discharge rod including, at a lower end, a plunger mounting portion to which a base end portion of the plunger is to be fitted; and the control unit moves the shaft member including the first cylindrical rod in the up-down direction so that the plunger mounted to the discharge rod reciprocates in the tubular passage in the syringe to suck the object into the tubular passage and discharge the sucked object.

4. A movement device, comprising:

a base;

the head device according to claim 1 arranged above the base;

a first container arranged at a first position on the base and configured to store an object;

a second container arranged at a second position on the base and configured to receive the object; and a head moving mechanism configured to move the head device in a horizontal direction between the first container and the second container.

\* \* \* \* \*